United States Patent [19]
Hlavka et al.

[11] Patent Number: 5,910,478
[45] Date of Patent: Jun. 8, 1999

[54] PEPTIDOMIMETICS INHIBITING THE ONCOGENIC ACTION OF P21 RAS

[75] Inventors: Joseph J. Hlavka, Tuxedo Park; John Fowler Noble, Pomona, both of N.Y.; Henry Baxter Abajian, Hillsdale, N.J.; Andrew S. Kende, Pittsford; Matthew R. Pincus, Brooklyn, both of N.Y.

[73] Assignee: Innapharma, Inc., Upper Saddle River, N.J.

[21] Appl. No.: 08/718,270

[22] Filed: Sep. 20, 1996

Related U.S. Application Data

[60] Provisional application No. 60/004,091, Sep. 21, 1995.
[51] Int. Cl.$^6$ .................................................... A61K 38/00
[52] U.S. Cl. ............................. 514/9; 514/12; 514/13; 514/14; 514/15; 514/16; 514/17; 514/18; 514/171; 514/169; 514/182; 552/575; 552/522
[58] Field of Search ......................... 514/9, 12–18, 514/171, 169, 182; 530/317, 324–331; 552/515, 522

[56] References Cited

U.S. PATENT DOCUMENTS 5,364,851  11/1994  Joran ........................................ 530/345

FOREIGN PATENT DOCUMENTS 0 203 587  12/1986  European Pat. Off. .
2694296   2/1994   France .
93/21314  10/1993  WIPO .

OTHER PUBLICATIONS

Brunwin et al. (1971) *J. Chem. Soc. C.* 3756.
Felix et al. (1978) *J. Org. Chem.* 43:4194.
Dueholm et al. (1993) *Org. Prep. Proc. Int.* 25:457.
Kohl et al. (1993) *Science* 260:1934–1937.
James et al. (1993) *Science* 260:1937–1942.
Chung et al. (1991) *Anticancer Res.* 11:1373–1942.
Chung et al. (1992) *Exp. Cell Res.* 203:329–335.
Hu et al. (1995) *Science* 268:100–102.
Pincus et al. (1992) *Ann. Clin. Lab. Sci. U.S.* 22:323–342.
Chung et al. (1992) *Biochem. Biophys. Res. Comm.* 181:1378–1384.
Haspel et al. (1992) *Med. Sci. Res.* 20:809–811.
Yamasaki et al. (1994) *Biochemistry* 33:65–73.

*Primary Examiner*—Sheela Huff
*Attorney, Agent, or Firm*—Greenlee, Winner and Sullivan, PC

[57] ABSTRACT

The present invention provides peptides, cyclized peptides and peptidomimetics which inhibit the oncogenic and/or transforming activity of the p21 ras protein, pharmaceutical compositions containing at least one of the ras-inhibiting peptides, cyclized peptides and peptidomimetics, and methods for inhibiting the ras-mediated oncogenic and/or transformation process in mammalian cells or tissues.

8 Claims, No Drawings

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
       (A) LENGTH: 6 amino acids
       (B) TYPE: amino acid
       (C) STRANDEDNESS:
       (D) TOPOLOGY: linear (ii) MOLECULE TYPE: peptide (iii) HYPOTHETICAL: NO (xi) SEQUENCE DESCRIPTION: SEQ ID NO:1:

Ile Lys Arg Val Lys Asp
   1               5

(2) INFORMATION FOR SEQ ID NO:2:

(i) SEQUENCE CHARACTERISTICS:
       (A) LENGTH: 5 amino acids
       (B) TYPE: amino acid
       (C) STRANDEDNESS: single
       (D) TOPOLOGY: linear (ii) MOLECULE TYPE: peptide (iii) HYPOTHETICAL: NO (xi) SEQUENCE DESCRIPTION: SEQ ID NO:2:

Lys Cys Asp Leu Ala
   1               5

(2) INFORMATION FOR SEQ ID NO:3:

(i) SEQUENCE CHARACTERISTICS:
       (A) LENGTH: 7 amino acids
       (B) TYPE: amino acid
       (C) STRANDEDNESS:
       (D) TOPOLOGY: linear (ii) MOLECULE TYPE: peptide (iii) HYPOTHETICAL: NO (xi) SEQUENCE DESCRIPTION: SEQ ID NO:3:

Cys Asp Leu Ala Ala Arg Thr

```
          1               5
```

(2) INFORMATION FOR SEQ ID NO:4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

```
   Asp Leu Ala Ala
   1
```

(2) INFORMATION FOR SEQ ID NO:5:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:5:

```
   Met Thr Glu Tyr Lys Leu Val Val Val Gly Ala Gly Gly Val Gly Lys
   1               5                  10                  15

Ser Ala Leu Thr Ile Gln Leu Ile Gln Asn His Phe Val Asp Glu Tyr
                  20                  25                  30

Asp Pro Thr Ile Glu Asp Ser Tyr Arg Lys Gln Val Val Ile Asp Gly
                  35                  40                  45

Glu Thr Cys Leu Leu Asp Ile Leu Asp Thr Ala Gly Gln Glu Glu Tyr
                  50                  55                  60

Ser Ala Met Arg Asp Gln Tyr Met Arg Thr Gly Glu Gly Phe Leu Cys
   65                  70                  75                  80

Val Phe Ala Ile Asn Asn Thr Lys Ser Phe Glu Asp Ile His Gln Tyr
                  85                  90                  95

Arg Glu Gln Ile Lys Arg Val Lys Asp Ser Asp Asp Val Pro Met Val
                  100                 105                 110

Leu Val Gly Asn Lys Cys Asp Leu Ala Ala Thr Val Glu Ser Arg Gln
                  115                 120                 125

Ala Gln Asp Leu Ala Arg Ser Tyr Gly Ile Pro Tyr Ile Glu Thr Ser
                  130                 135                 140

Ala Lys Thr Arg Gln Gly Val Glu Asp Ala Phe Tyr Thr Leu Val Arg
   145                 150                 155                 160

Glu Ile Arg Gln His Lys Leu Arg Lys Leu Asn Pro Pro Asp Glu Ser
                  165                 170                 175

Gly Pro Gly Cys Met Ser Cys Lys Cys Val Leu Ser
                  180                 185
```

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:6:

Thr Ile Glu Asp Ser Tyr Arg Lys Gln Val Val Ile Asp
    1               5                  10

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:7:

Tyr Arg Glu Gln Ile Lys Arg Val Lys Asp Ser Asp Val Pro
    1               5                  10                  15

(2) INFORMATION FOR SEQ ID NO:8:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:8:

Gly Asn Lys Cys Asp Leu Ala Ala Arg Thr Val Glu
    1               5                  10

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:9:

Cys Asp Leu Ala Ala Arg Thr
    1               5

(2) INFORMATION FOR SEQ ID NO:10:

(i) SEQUENCE CHARACTERISTICS:
        (A) LENGTH: 215 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Arabidopsis thaliana (xi) SEQUENCE DESCRIPTION: SEQ ID NO:10:

```
Met Ala Ala Pro Pro Ala Arg Ala Arg Ala Asp Tyr Asp Tyr Leu Ile
1               5                   10                  15

Lys Leu Leu Leu Ile Gly Asp Ser Gly Val Gly Lys Ser Cys Leu Leu
                20                  25                  30

Leu Arg Phe Ser Asp Gly Ser Phe Thr Thr Ser Phe Ile Thr Thr Ile
            35                  40                  45

Gly Ile Asp Phe Lys Ile Arg Thr Ile Glu Leu Asp Gly Lys Arg Ile
50                  55                  60

Lys Leu Gln Ile Trp Asp Thr Ala Gly Gln Glu Arg Arg Thr Ile Thr
65                  70                  75                  80

Thr Ala Tyr Tyr Arg Gly Ala Met Gly Ile Leu Leu Val Tyr Asp Val
                85                  90                  95

Thr Asp Glu Ser Ser Phe Asn Asn Ile Arg Asn Trp Ile Arg Asn Ile
                100                 105                 110

Glu Gln His Ala Ser Asp Asn Val Asn Lys Ile Leu Val Gly Asn Lys
            115                 120                 125

Ala Asp Met Asp Glu Ser Lys Arg Ala Val Pro Thr Ala Lys Gly Gln
130                 135                 140

Ala Leu Ala Asp Glu Tyr Gly Ile Lys Phe Phe Glu Thr Ser Ala Lys
145                 150                 155                 160

Thr Asn Leu Asn Val Glu Glu Val Phe Phe Ser Ile Gly Arg Asp Ile
                165                 170                 175

Lys Gln Arg Leu Ser Asp Thr Asp Ser Arg Ala Glu Pro Ala Thr Ile
            180                 185                 190

Lys Ile Ser Gln Thr Asp Gln Ala Ala Gly Ala Gly Gln Ala Thr Gln
            195                 200                 205

Lys Ser Ala Cys Cys Gly Thr
210                 215
```

(2) INFORMATION FOR SEQ ID NO:11:

(i) SEQUENCE CHARACTERISTICS:
        (A) LENGTH: 213 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Arabidopsis thaliana (xi) SEQUENCE DESCRIPTION: SEQ ID NO:11:

```
Met Ala Gly Tyr Ala Asp Glu Glu Tyr Asp Tyr Leu Phe Lys Leu Val
1               5                   10                  15

Leu Ile Gly Asp Ser Gly Val Gly Lys Ser Asn Leu Leu Ser Arg Phe
                20                  25                  30

Thr Lys Asn Phe Asn Leu Glu Ser Lys Ser Thr Ile Gly Val Glu Phe
            35                  40                  45

Ala Thr Lys Thr Thr Lys Val Glu Gly Lys Val Val Lys Ala Gln Ile
50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Ile Tyr Asp Val Thr Arg His
                85                  90                  95

Ala Thr Phe Glu Asn Ala Ala Arg Trp Leu Arg Glu Leu Arg Gly His
```

```
                  100                 105                 110
    Thr Asp Pro Asn Ile Val Val Met Leu Ile Gly Asn Lys Cys Asp Leu
                115                 120                 125

Arg His Leu Val Ala Val Lys Thr Glu Glu Ala Lys Ala Phe Ala Glu
    130                 135                 140

Arg Glu Ser Leu Tyr Phe Met Glu Thr Ser Ala Leu Asp Ala Thr Asn
    145                 150                 155                 160

Val Glu Asn Ala Phe Thr Glu Val Leu Thr Gln Ile His Lys Ile Val
                    165                 170                 175

Ser Lys Arg Ser Val Asp Gly Gly Ser Ala Asp Leu Pro Gly Lys
                180                 185                 190

Gly Glu Thr Ile Asn Val Lys Glu Asp Gly Ser Val Leu Lys Arg Met
                195                 200                 205

Gly Cys Cys Ser Asn
                210
```

(2) INFORMATION FOR SEQ ID NO:12:

(i) SEQUENCE CHARACTERISTICS:
        (A) LENGTH: 213 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Arabidopsis thaliana (xi) SEQUENCE DESCRIPTION: SEQ ID NO:12:

```
    Met Ser Ser Asp Asp Glu Gly Arg Glu Glu Tyr Phe Lys Ile Val Val
    1               5                   10                  15

Ile Gly Asp Ser Ala Val Gly Lys Ser Asn Leu Leu Ser Arg Tyr Ala
                    20                  25                  30

Arg Asn Glu Phe Ser Ala Asn Ser Lys Ala Thr Ile Gly Val Glu Phe
                35                  40                  45

Gln Thr Gln Ser Met Ile Glu Gly Lys Glu Val Lys Ala Gln Ile Trp
            50                  55                  60

Asp Thr Ala Gly Gln Glu Phe Arg Ala Val Thr Ser Tyr Tyr Arg Gly
    65                  70                  75                  80

Ala Val Gly Ala Leu Val Val Tyr Asp Ile Thr Arg Arg Thr Thr Phe
                    85                  90                  95

Glu Ser Val Gly Arg Trp Leu Asp Glu Leu Lys Ile His Ser Asp Thr
                100                 105                 110

Thr Val Ala Arg Met Leu Val Gly Asn Lys Cys Asp Leu Glu Asn Ile
                115                 120                 125

Arg Ala Val Ser Val Glu Glu Gly Lys Ala Leu Ala Glu Glu Glu Gly
    130                 135                 140

Leu Phe Phe Val Glu Thr Ser Ala Leu Asp Ser Thr Asn Val Lys Thr
    145                 150                 155                 160

Ala Phe Glu Met Val Ile Leu Asp Ile Tyr Asn Asn Val Ser Arg Lys
                    165                 170                 175

Gln Leu Asn Ser Asp Thr Tyr Lys Asp Glu Leu Thr Val Arg Val Ser
                180                 185                 190

Leu Val Lys Asp Asp Asn Ser Ala Ser Lys Gln Ser Ser Gly Phe Ser
                195                 200                 205
```

-continued

```
        Cys Cys Ser Ser Thr
                210
```

(2) INFORMATION FOR SEQ ID NO:13:

(i) SEQUENCE CHARACTERISTICS:
        (A) LENGTH: 201 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Discopyge ommata (xi) SEQUENCE DESCRIPTION: SEQ ID NO:13:

```
Met Asn Pro Glu Tyr Asp Tyr Leu Phe Lys Leu Leu Ile Gly Asp
 1               5                  10                  15

Ser Gly Val Gly Lys Ser Cys Leu Leu Leu Arg Phe Ala Asp Asp Thr
                20                  25                  30

Tyr Thr Glu Ser Tyr Ile Ser Thr Ile Gly Val Asp Phe Lys Ile Arg
                35                  40                  45

Thr Ile Glu Leu Asp Gly Lys Thr Ile Lys Leu Gln Ile Trp Asp Thr
        50                  55                  60

Ala Gly Gln Glu Arg Phe Arg Thr Ile Thr Ser Ser Tyr Tyr Arg Gly
65                  70                  75                  80

Ala His Gly Ile Ile Val Val Tyr Asp Val Thr Asp Gln Glu Ser Phe
                85                  90                  95

Asn Asn Val Lys Gln Trp Leu Gln Glu Ile Asp Arg Tyr Ala Ser Glu
                100                 105                 110

Asn Val Asn Lys Leu Leu Val Gly Asn Lys Cys Asp Leu Thr Thr Lys
                115                 120                 125

Lys Val Val Asp Tyr Thr Thr Lys Glu Phe Ala Asp Ser Leu Gly Ile
            130                 135                 140

Pro Phe Leu Glu Thr Ser Ala Lys Asn Ala Thr Asn Val Glu Gln Ala
145                 150                 155                 160

Phe Met Thr Met Ala Ala Glu Ile Lys Lys Arg Met Gly Pro Gly Ala
                165                 170                 175

Thr Ser Gly Gly Ser Glu Lys Ser Asn Val Asn Ile Gln Ser Thr Pro
                180                 185                 190

Val Lys Ser Ser Gly Gly Gly Cys Cys
            195                 200
```

(2) INFORMATION FOR SEQ ID NO:14:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Lymnea stagnalis (xi) SEQUENCE DESCRIPTION: SEQ ID NO:14:

```
Met Ser Thr Met Asn Pro Asp Tyr Asp Tyr Leu Phe Lys Leu Leu Leu
 1               5                  10                  15
```

```
    Ile Gly Asp Ser Gly Val Gly Lys Ser Cys Leu Leu Leu Arg Phe Ala
                 20                  25                  30

Asp Asp Thr Tyr Thr Glu Ser Tyr Ile Ser Thr Ile Gly Val Asp Phe
                 35                  40                  45

Lys Ile Arg Thr Ile Glu Leu Asp Gly Lys Thr Ile Lys Leu Gln Ile
     50                  55                  60

Trp Asp Thr Ala Gly Gln Glu Arg Phe Arg Thr Ile Thr Ser Ser Tyr
     65                  70                  75                  80

Tyr Arg Gly Ala His Gly Ile Ile Val Val Tyr Asp Val Thr Asp Gln
                     85                  90                  95

Glu Ser Phe Asn Asn Val Lys Gln Trp Leu Gln Glu Ile Asp Arg Tyr
                    100                 105                 110

Ala Ser Glu Asn Val Asn Lys Leu Leu Val Gly Asn Lys Ser Asp Leu
                    115                 120                 125

Thr Thr Lys Lys Val Asp Phe Thr Thr Ala Lys Glu Tyr Ala Asp Gln
                130                 135                 140

Leu Gly Ile Pro Phe Leu Glu Thr Ser Ala Lys Asn Ala Thr Asn Val
    145                 150                 155                 160

Glu Gln Ala Phe Met Thr Met Ala Ala Glu Ile Lys Asn Arg Met Gly
                    165                 170                 175

Pro Ile Thr Ala Ser Asp Ser Lys Pro Ser Val Lys Ile Asn Ser Ser
                    180                 185                 190

Thr Pro Ser Ala Asn Lys Gly Gly Cys Cys
                    195                 200

(2) INFORMATION FOR SEQ ID NO:15:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:15:

Met Ala Tyr Ala Tyr Leu Phe Lys Tyr Ile Ile Ile Gly Asp Thr Gly
     1               5                  10                  15

Val Gly Lys Ser Cys Leu Leu Leu Gln Phe Thr Asp Lys Arg Phe Gln
                 20                  25                  30

Pro Val His Asp Leu Thr Ile Gly Val Glu Phe Gly Ala Arg Met Ile
                 35                  40                  45

Thr Ile Asp Gly Lys Gln Ile Lys Leu Gln Ile Trp Asp Thr Ala Gly
     50                  55                  60

Gln Glu Ser Phe Arg Ser Ile Thr Arg Ser Tyr Tyr Arg Gly Ala Ala
     65                  70                  75                  80

Gly Ala Leu Leu Val Tyr Asp Ile Thr Arg Arg Asp Thr Phe Asn His
                     85                  90                  95

Leu Thr Thr Trp Leu Glu Asp Ala Arg Gln His Ser Asn Ser Asn Met
                    100                 105                 110

Val Ile Met Leu Ile Gly Asn Lys Ser Asp Leu Glu Arg Arg Glu Val
                    115                 120                 125

Lys Lys Glu Glu Gly Glu Ala Phe Ala Glu His Gly Leu Ile Phe Met
```

```
                    130                 135                 140
        Glu Thr Ala Lys Thr Ala Ser Val Glu Glu Ala Phe Ile Asn Thr Ala
        145                 150                 155                 160

Lys Glu Ile Tyr Glu Lys Ile Gln Glu Val Phe Asp Ile Asn Asn
                        165                 170                 175

Glu Ala Asn Gly Ile Lys Ile Gly Pro Gln His Ala Ala Thr Asn Ala
                        180                 185                 190

Thr His Ala Gly Asn Gln Gly Gly Gln Gln Ala Gly Gly Cys Cys
                    195                 200                 205
```

(2) INFORMATION FOR SEQ ID NO:16:

(i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Lymnea stagnalis (xi) SEQUENCE DESCRIPTION: SEQ ID NO:16:

```
        Met Ser Tyr Ala Tyr Leu Phe Lys Tyr Ile Ile Ile Gly Asp Thr Gly
        1               5                   10                  15

Val Gly Lys Ser Cys Leu Leu Leu Gln Phe Thr Asp Lys Arg Phe Gln
                        20                  25                  30

Pro Val His Asp Leu Thr Ile Gly Val Glu Phe Gly Ala Arg Met Ile
                        35                  40                  45

Thr Ile Asp Gly Lys Gln Ile Lys Leu Gln Ile Trp Asp Thr Ala Gly
        50                  55                  60

Gln Glu Ser Phe Arg Ser Ile Thr Arg Ser Tyr Tyr Arg Gly Ala Ala
        65                  70                  75                  80

Gly Ala Leu Leu Val Tyr Asp Ile Thr Arg Arg Asp Thr Phe Asn His
                        85                  90                  95

Leu Thr Thr Trp Leu Glu Asp Ala Arg Gln His Ser Asn Ser Asn Met
                        100                 105                 110

Val Ile Met Leu Ile Gly Asn Lys Ser Asp Leu Glu Ala Arg Arg Val
                        115                 120                 125

Lys Lys Glu Glu Gly Glu Ala Phe Arg Glu His Gly Leu Ile Phe Met
        130                 135                 140

Glu Thr Ser Ala Lys Thr Ala Ala Asn Val Glu Glu Ala Phe Ile Asn
        145                 150                 155                 160

Thr Ala Lys Glu Ile Tyr Gln Lys Ile Gln Asp Gly Val Phe Asp Ile
                        165                 170                 175

Asn Asn Glu Ala Asn Gly Ile Lys Ile Gly Pro Gln His Ser Pro Ala
                        180                 185                 190

Ser Gln Ser Leu Asn Val Gly Gly Ser Gly Gly Asn Gln Gly Gly Asn
                    195                 200                 205

Cys Cys
            210
```

(2) INFORMATION FOR SEQ ID NO:17:

(i) SEQUENCE CHARACTERISTICS:
        (A) LENGTH: 208 amino acids
        (B) TYPE: amino acid (C) STRANDEDNESS: single
            (D) TOPOLOGY: linear (ii) MOLECULE TYPE: protein (iii) HYPOTHETICAL: NO (vi) ORIGINAL SOURCE:
          (A) ORGANISM: Oryctolagus cuniculus (xi) SEQUENCE DESCRIPTION: SEQ ID NO:17:

Met Ala Tyr Ala Tyr Leu Phe Lys Tyr Ile Ile Ile Gly Asp Thr Gly
    1               5                   10                  15

Val Gly Lys Ser Cys Leu Leu Leu Gln Phe Thr Asp Lys Arg Phe Gln
                    20                  25                  30

Pro Val His Asp Leu Thr Ile Gly Val Glu Phe Gly Ala Arg Met Ile
                35                  40                  45

Thr Ile Asp Gly Lys Gln Ile Lys Leu Gln Ile Trp Asp Thr Ala Gln
    50                  55                  60

Glu Ser Phe Arg Ser Ile Arg Ser Tyr Tyr Arg Gly Ala Gly Ala Leu
    65                  70                  75                  80

Leu Val Tyr Asp Ile Thr Arg Arg Asp Thr Phe Asn His Leu Thr Thr
                    85                  90                  95

Trp Leu Glu Asp Ala Arg Gln His Ser Asn Ser Asn Met Val Ile Met
                    100                 105                 110

Leu Ile Gly Asn Lys Ser Asp Leu Glu Ser Arg Arg Glu Val Lys Lys
                    115                 120                 125

Glu Glu Gly Glu Ala Phe Ala Arg Glu His Gly Leu Ile Phe Met Glu
                    130                 135                 140

Thr Ser Ala Lys Thr Ala Ser Asn Val Glu Glu Ala Phe Ile Asn Thr
    145                 150                 155                 160

Ala Lys Glu Ile Tyr Glu Lys Ile Gln Glu Gly Val Phe Asp Ile Asn
                        165                 170                 175

Asn Glu Ala Asn Gly Ile Lys Ile Gly Pro Gln His Gly Ala Thr Asn
                    180                 185                 190

Ala His Ala Gly Asn Gln Gly Gln Gln Ala Gly Gly Gly Cys Cys
                    195                 200                 205

(2) INFORMATION FOR SEQ ID NO:18:

(i) SEQUENCE CHARACTERISTICS:
        (A) LENGTH: 212 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
          (A) ORGANISM: Rattus norvegicus (xi) SEQUENCE DESCRIPTION: SEQ ID NO:18:

Met Ala Tyr Ala Tyr Leu Phe Lys Tyr Ile Ile Ile Gly Asp Thr Gly
    1               5                   10                  15

Val Gly Lys Ser Cys Leu Leu Leu Gln Phe Thr Asp Lys Arg Phe Gln
                    20                  25                  30

Pro Val His Asp Leu Thr Met Gly Val Glu Phe Gly Ala Arg Met Ile
                35                  40                  45

Thr Ile Asp Gly Lys Gln Ile Lys Leu Gln Ile Trp Asp Thr Ala Gly
    50                  55                  60

```
Gln Glu Ser Phe Arg Ser Ile Thr Arg Ser Tyr Tyr Arg Gly Ala Ala
 65                  70                  75                  80

Gly Ala Leu Leu Val Tyr Asp Ile Thr Arg Arg Asp Thr Phe Asn His
             85                  90                  95

Leu Thr Thr Trp Leu Glu Asp Ala Arg Gln His Ser Asn Ser Asn Met
            100                 105                 110

Val Ile Met Leu Ile Gly Asn Lys Ser Asp Leu Glu Ser Arg Arg Glu
        115                 120                 125

Val Lys Lys Glu Glu Gly Glu Ala Phe Ala Arg Glu His Gly Leu Ile
    130                 135                 140

Phe Met Glu Thr Ser Ala Lys Thr Ala Ser Asn Val Glu Glu Ala Phe
145                 150                 155                 160

Ile Asn Thr Ala Lys Glu Ile Tyr Glu Lys Ile Gln Glu Gly Val Phe
                165                 170                 175

Asp Ile Asn Asn Glu Ala Asn Gly Ile Lys Ile Gly Pro Gln His Ala
            180                 185                 190

Ala Thr Asn Ala Ser His Gly Gly Asn Gln Gly Gly Gln Gln Ala Gly
        195                 200                 205

Gly Gly Cys Cys
    210
```

(2) INFORMATION FOR SEQ ID NO:19:

(i) SEQUENCE CHARACTERISTICS:
      (A) LENGTH: 218 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
       (A) ORGANISM: Drosophila melanogaster (xi) SEQUENCE DESCRIPTION: SEQ ID NO:19:

```
Met Ala Gly Gly Asp Pro Lys Trp Gln Lys Asp Ala Ala Asp Gln Asn
  1              5                  10                  15

Phe Asp Tyr Met Phe Lys Leu Leu Ile Ile Gly Asn Ser Ser Val Gly
             20                  25                  30

Lys Thr Ser Phe Leu Phe Arg Tyr Ala Asp Asp Ser Phe Thr Ser Ala
             35                  40                  45

Phe Val Ser Thr Val Gly Ile Asp Phe Lys Val Lys Thr Val Phe Arg
     50                  55                  60

His Asp Lys Arg Val Lys Leu Gln Ile Trp Asp Thr Ala Gly Gln Glu
 65                  70                  75                  80

Arg Tyr Arg Thr Ile Thr Thr Ala Tyr Tyr Arg Gly Ala Met Gly Phe
             85                  90                  95

Ile Leu Met Tyr Asp Val Thr Asn Glu Asp Ser Phe Asn Ser Val Gln
            100                 105                 110

Asp Trp Val Thr Gln Ile Lys Thr Tyr Ser Trp Asp Asn Ala Gln Val
        115                 120                 125

Ile Leu Val Gly Asn Lys Cys Asp Met Glu Asp Gln Arg Val Ile Ser
    130                 135                 140

Phe Glu Arg Gly Arg Gln Leu Ala Asp Gln Leu Gly Val Glu Phe Phe
145                 150                 155                 160

Glu Thr Ser Ala Lys Glu Asn Val Asn Val Lys Ala Val Phe Glu Arg
```

```
              165                 170                 175
    Leu Val Asp Ile Ile Cys Lys Met Ser Glu Ser Leu Asp Ala Asp Pro
                    180                 185                 190

Thr Leu Val Gly Gly Gly Gln Lys Gly Gln Arg Leu Thr Asp Gln Pro
            195                 200                 205

Gln Gly Thr Pro Asn Ala Asn Cys Asn Cys
            210                 215
```

(2) INFORMATION FOR SEQ ID NO:20:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Rattus norvegicus (xi) SEQUENCE DESCRIPTION: SEQ ID NO:20:

```
    Met Ser Glu Thr Tyr Asp Phe Leu Lys Phe Leu Val Ile Gly Asn Ala
    1               5                   10                  15

Gly Thr Gly Lys Ser Cys Leu Leu His Gln Phe Ile Glu Lys Lys Phe
                    20                  25                  30

Lys Asp Asp Ser Asn His Thr Ile Gly Val Glu Phe Gly Gln Lys Ile
                35                  40                  45

Ile Asn Val Gly Gly Lys Tyr Val Lys Leu Gln Ile Trp Asp Thr Ala
    50                  55                  60

Gly Gln Glu Arg Phe Arg Val Thr Thr Ser Tyr Arg Gly Ala Ala Gly
    65                  70                  75                  80

Ala Leu Leu Val Tyr Asp Ile Thr Ser Arg Glu Thr Tyr Asn Ala Leu
                    85                  90                  95

Thr Asn Trp Leu Thr Asp Ala Arg Met Leu Ala Ser Gln Asn Ile Val
                    100                 105                 110

Ile Cys Gly Asn Lys Lys Asp Leu Asp Ala Asp Arg Glu Val Thr Phe
                    115                 120                 125

Leu Glu Ala Ser Arg Phe Ala Gln Glu Asn Glu Leu Met Phe Leu Glu
            130                 135                 140

Thr Ser Ala Leu Thr Gly Glu Asn Val Glu Glu Ala Phe Met Gln Cys
    145                 150                 155                 160

Ala Arg Lys Ile Leu Asn Lys Ile Glu Ser Gly Glu Leu Asp Pro Glu
                    165                 170                 175

Arg Met Gly Ser Gly Ile Gln Tyr Gly Asp Ala Ala Leu Arg Gln Leu
                    180                 185                 190

Arg Ser Pro Arg Arg Thr Gln Ala Pro Ser Ala Gln Glu Cys Gly Cys
            195                 200                 205
```

(2) INFORMATION FOR SEQ ID NO:21:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (A) ORGANISM: Caenorhabditis elegans (xi) SEQUENCE DESCRIPTION: SEQ ID NO:21:

```
Met Ala Asp Phe Thr Asn Asn Ala Leu Lys Lys Phe Lys Leu Val Phe
1               5                   10                  15

Leu Gly Glu Gln Ser Val Gly Lys Thr Ser Ile Ile Thr Arg Phe Met
            20                  25                  30

Tyr Asp Ser Phe Asp Asn Thr Tyr Gln Ala Thr Ile Gly Ile Asp Phe
        35                  40                  45

Leu Ser Lys Thr Met Tyr Leu Glu Asp Arg Thr Ile Arg Leu Gln Leu
    50                  55                  60

Trp Asp Thr Ala Gly Gln Glu Arg Phe Arg Ser Leu Ile Pro Ser Tyr
65                  70                  75                  80

Ile Arg Asp Ser Ser Val Ala Val Val Tyr Asp Ile Thr Asn Ala
                85                  90                  95

Asn Ser Phe His Gln Thr Thr Lys Trp Val Asp Asp Val Arg Asn Glu
                100                 105                 110

Arg Gly Cys Asp Val Ile Ile Val Leu Val Gly Asn Lys Thr Asp Leu
            115                 120                 125

Ala Asp Lys Arg Gln Val Ser Thr Glu Asp Gly Glu Lys Lys Ala Arg
130                 135                 140

Asp Leu Asn Val Met Phe Ile Glu Thr Ser Ala Lys Ala Gly Tyr Asn
145                 150                 155                 160

Val Lys Gln Leu Phe Arg Lys Ile Ala Leu Pro Gly Ile Val Gln Glu
                165                 170                 175

Glu Thr Pro Glu Gln Pro Asn Ile Val Ile Met Asn Pro Lys Asp
            180                 185                 190

Ala Glu Glu Ser Gln Gly Arg Gln Cys Pro Cys
            195                 200
```

(2) INFORMATION FOR SEQ ID NO:22:

(i) SEQUENCE CHARACTERISTICS:
       (A) LENGTH: 207 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Homo sapiens (xi) SEQUENCE DESCRIPTION: SEQ ID NO:22:

```
Met Ser Thr Gly Gly Asp Phe Gly Asn Pro Leu Arg Lys Phe Lys Leu
1               5                   10                  15

Val Phe Leu Gly Glu Gln Ser Val Gly Lys Thr Ser Leu Ile Thr Arg
            20                  25                  30

Phe Met Tyr Asp Ser Phe Asp Asn Thr Tyr Gln Ala Thr Ile Gly Ile
        35                  40                  45

Asp Phe Leu Ser Lys Thr Met Tyr Leu Glu Asp Arg Thr Val Arg Leu
    50                  55                  60

Gln Leu Trp Asp Thr Ala Gly Gln Glu Arg Phe Arg Ser Leu Ile Pro
65                  70                  75                  80

Ser Tyr Ile Arg Asp Ser Thr Val Ala Val Val Val Tyr Asp Ile Thr
                85                  90                  95
```

```
Asn Val Asn Ser Phe Gln Gln Thr Thr Lys Trp Ile Asp Asp Val Arg
                100                 105                 110

Thr Glu Arg Gly Ser Asp Val Ile Ile Met Leu Val Gly Asn Lys Thr
        115                 120                 125

Asp Leu Ala Asp Lys Arg Gln Val Ser Ile Glu Glu Gly Glu Arg Lys
    130                 135                 140

Ala Lys Glu Leu Asn Val Met Phe Ile Glu Ser Ala Lys Ala Gly Tyr
145                 150                 155                 160

Asn Val Lys Gln Leu Phe Arg Arg Val Ala Ala Leu Pro Gly Met
                165                 170                 175

Glu Ser Thr Gln Asp Arg Ser Arg Glu Asp Met Ile Asp Ile Lys Leu
            180                 185                 190

Glu Lys Pro Gln Glu Gln Pro Val Ser Glu Gly Gly Cys Ser Cys
        195                 200                 205
```

(2) INFORMATION FOR SEQ ID NO:23:

(i) SEQUENCE CHARACTERISTICS:
      (A) LENGTH: 203 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: Canis familiaris (xi) SEQUENCE DESCRIPTION: SEQ ID NO:23:

```
Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
50                  55                  60

Ala Gly Gln Glu Arg Phe Gln Ser Leu Gly Val Phe Tyr Arg Gly Ala
65                  70                  75                  80

Asp Cys Cys Val Leu Val Phe Asp Val Thr Ala Pro Asn Thr Phe Lys
                85                  90                  95

Thr Leu Asp Ser Trp Arg Asp Glu Phe Leu Ile Gln Ala Ser Pro Arg
                100                 105                 110

Asp Pro Glu Asn Phe Pro Phe Val Val Leu Gly Asn Lys Ile Asp Leu
            115                 120                 125

Glu Asn Arg Gln Val Ala Thr Lys Arg Ala Gln Ala Trp Cys Tyr Ser
    130                 135                 140

Lys Asn Asn Ile Pro Tyr Phe Glu Thr Ser Ala Lys Glu Ala Ile Asn
145                 150                 155                 160

Val Glu Gln Ala Phe Gln Thr Ile Ala Arg Asn Ala Leu Lys Gln Glu
                165                 170                 175

Thr Glu Val Glu Leu Tyr Asn Glu Phe Pro Glu Pro Ile Lys Leu Asp
            180                 185                 190

Lys Asp Ala Lys Thr Ser Ala Glu Cys Ser Cys
        195                 200
```

(2) INFORMATION FOR SEQ ID NO:24:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:24:

```
Met Thr Lys Lys Val Leu Leu Lys Val Ile Ile Leu Gly Asp Ser
 1               5                  10                  15

Gly Val Gly Lys Thr Ser Leu Met Asn Gln Tyr Val Asn Lys Lys Phe
            20                  25                  30

Ser Asn Gln Tyr Lys Ala Thr Ile Gly Ala Asp Phe Leu Thr Lys Glu
        35                  40                  45

Leu Met Val Asp Asp Arg Val Val Thr Met Gln Ile Trp Asp Thr Ala
50                  55                  60

Gly Gln Glu Arg Phe Gln Ser Leu Gly Val Ala Phe Tyr Arg Gly Ala
65                  70                  75                  80

Asp Cys Cys Val Leu Cys Tyr Asp Val Asn Val Ala Lys Thr Phe Glu
                    85                  90                  95

Asn Leu Asp Ser Trp Arg Asp Glu Phe Leu Ile Gln Ala Gly Pro Arg
                100                 105                 110

Asp Pro Asp Asn Phe Pro Phe Val Val Leu Gly Asn Lys Ile Asp Leu
            115                 120                 125

Glu Asn Gln Arg Val Val Ser Gln Lys Arg Ala Ala Ser Trp Cys Gln
130                 135                 140

Ser Lys Gly Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Ile Lys Leu
                    165                 170                 175

Glu Asp Gly Leu Val Phe Pro Ile Pro Thr Asn Ile Gly Val Ile Pro
                180                 185                 190

Glu Pro Gln Pro Ala Lys Ser Gly Cys Cys
            195                 200
```

(2) INFORMATION FOR SEQ ID NO:25:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Canis familiaris (xi) SEQUENCE DESCRIPTION: SEQ ID NO:25:

```
Met Lys Thr Tyr Asp Tyr Leu Phe Lys Leu Leu Leu Ile Gly Asp Ser
 1               5                  10                  15

Gly Val Gly Lys Thr Cys Val Leu Phe Arg Phe Ser Glu Asp Ala Phe
            20                  25                  30
```

```
        Asn Ser Thr Phe Ile Ser Thr Ile Gly Ile Asp Phe Lys Ile Arg Thr
                 35                  40                  45

Ile Glu Leu Asp Gly Lys Arg Ile Lys Leu Gln Ile Trp Asp Thr Ala
         50                  55                  60

Gly Gln Glu Arg Phe Arg Thr Ile Thr Thr Ala Tyr Tyr Arg Ala Met
         65                  70                  75                  80

Gly Ile Met Leu Val Tyr Asp Ile Thr Asn Glu Lys Ser Phe Asp Asn
                             85                  90                  95

Ile Arg Asn Trp Ile Arg Asn Ile Glu Glu His Ala Ser Ala Asp Val
                        100                 105                 110

Glu Lys Met Ile Leu Gly Asn Lys Cys Asp Val Asn Asp Lys Arg Gln
                    115                 120                 125

Val Ser Lys Glu Arg Gly Glu Lys Leu Ala Leu Asp Tyr Gly Ile Lys
        130                 135                 140

Phe Met Glu Thr Ser Ala Lys Ala Asn Ile Asn Val Glu Asn Ala Phe
        145                 150                 155                 160

Phe Thr Leu Ala Arg Asp Ile Lys Ala Lys Met Asp Lys Lys Leu Glu
                            165                 170                 175

Gly Asn Ser Pro Gln Gly Ser Asn Gln Gly Val Lys Ile Thr Pro Asp
                        180                 185                 190

Gln Gln Lys Arg Ser Ser Phe Phe Arg Cys Val Leu Leu
                    195                 200                 205

(2) INFORMATION FOR SEQ ID NO:26:

(i) SEQUENCE CHARACTERISTICS:
        (A) LENGTH: 191 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:26:

Met Glu Glu Glu Ile Leu Tyr Lys Ile Ile Leu Val Gly Glu Ser Gly
          1               5                  10                  15

Val Gly Lys Ser Ser Ile Leu Val Arg Phe Thr Asp Asn Thr Phe Ser
                         20                  25                  30

Gln His Phe Ala Pro Thr Leu Gly Val Phe Val Lys Thr Ile Arg Asn
                     35                  40                  45

Lys Glu Thr Gly Gln Thr Val Lys Leu Gln Leu Trp Asp Thr Ala Gly
         50                  55                  60

Gln Glu Arg Phe Lys Ser Ile Thr Gln Phe Tyr Arg Gly Ser His Gly
         65                  70                  75                  80

Val Ile Val Val Tyr Asp Val Thr Asp Pro Lys Ser Phe Glu Arg Leu
                             85                  90                  95

Lys Asn Trp Val Glu Asp Ile Asn Gln Tyr Thr Gln Asp Gly Met Ile
                        100                 105                 110

Ile Ile Leu Val Gly Asn Lys Ser Asp Met Val Ala Gln Arg Lys Val
                    115                 120                 125

Thr Phe Glu Gln Gly Gln Glu Met Ala Glu Gln Leu Lys Thr Lys Phe
        130                 135                 140

Leu Glu Val Ser Ala Lys Glu Asn Asn Gly Val Thr Gln Val Phe Asp
        145                 150                 155                 160
```

```
        Leu Leu Val Gln Asp Ile Glu Ala Thr Met Lys Asn Ser Lys Val Ala
                        165                 170                 175

Gln Asn Gln Leu Asn Leu Ser Val Gly Gln Glu Arg Gly Cys Cys
                    180                 185                 190

(2) INFORMATION FOR SEQ ID NO:27:

(i) SEQUENCE CHARACTERISTICS:
         (A) LENGTH: 189 amino acids
         (B) TYPE: amino acid
         (C) STRANDEDNESS: single
         (D) TOPOLOGY: linear (ii) MOLECULE TYPE: protein (iii) HYPOTHETICAL: NO (vi) ORIGINAL SOURCE:
         (A) ORGANISM: Caenorhabditis elegans (xi) SEQUENCE DESCRIPTION: SEQ ID NO:27:

Met Gln Ala Ile Lys Cys Val Val Gly Asp Gly Ala Val Gly Lys
        1               5                   10                  15

Thr Cys Leu Leu Ile Ser Tyr Thr Thr Asn Ala Phe Pro Gly Glu Tyr
                        20                  25                  30

Ile Pro Thr Val Phe Asp Asn Tyr Ser Ala Asn Val Met Val Asp Gly
                        35                  40                  45

Arg Pro Ile Asn Leu Gly Leu Trp Asp Thr Ala Gly Gln Asp Tyr Asp
                        50                  55                  60

Arg Leu Arg Pro Leu Ser Tyr Pro Gln Thr Asp Val Phe Leu Val Cys
        65                  70                  75                  80

Phe Ala Leu Asn Asn Pro Ala Ser Phe Glu Asn Val Arg Ala Lys Trp
                        85                  90                  95

Tyr Pro Glu Val Ser His His Cys Pro Asn Thr Pro Ile Ile Leu Val
                        100                 105                 110

Gly Thr Lys Ala Asp Leu Arg Glu Asp Asp Thr Val Glu Arg Leu Arg
                        115                 120                 125

Glu Arg Arg Leu Gln Pro Val Ser Gln Thr Gln Gly Tyr Val Met Ala
                        130                 135                 140

Lys Glu Ile Lys Ala Val Lys Tyr Leu Glu Cys Ser Ala Leu Thr Gln
        145                 150                 155                 160

Arg Gly Leu Lys Gln Val Phe Asp Glu Ala Ile Arg Ala Val Val Thr
                        165                 170                 175

Pro Pro Gln Arg Ala Lys Lys Ser Lys Cys Thr Val Leu
                        180                 185

(2) INFORMATION FOR SEQ ID NO:28:

(i) SEQUENCE CHARACTERISTICS:
         (A) LENGTH: 191 amino acids
         (B) TYPE: amino acid
         (C) STRANDEDNESS: single
         (D) TOPOLOGY: linear (ii) MOLECULE TYPE: protein (iii) HYPOTHETICAL: NO (vi) ORIGINAL SOURCE:
         (A) ORGANISM: Dictyostelium discoideum (xi) SEQUENCE DESCRIPTION: SEQ ID NO:28:

Met Gln Ala Ile Lys Cys Val Val Val Gly Asp Gly Ala Val Gly Lys
```

```
             1               5                  10                 15
         Thr Cys Leu Leu Ile Ser Tyr Thr Thr Asn Ala Phe Pro Gly Glu Tyr
                         20                  25                  30

Ile Pro Thr Val Phe Asp Asn Tyr Ser Ala Asn Val Met Val Asp Gly
                         35                  40                  45

Lys Pro Ile Asn Leu Gly Leu Trp Asp Thr Ala Gly Gln Glu Asp Tyr
                         50                  55                  60

Asp Arg Leu Arg Pro Leu Ser Tyr Pro Gln Thr Asp Val Phe Leu Ile
         65                      70                  75                  80

Cys Phe Ser Ile Ile Ser Pro Ser Phe Glu Asn Val Asn Gly Lys
                                 85                  90                  95

Trp His Pro Glu Ile Cys His His Pro Asn Val Pro Ile Leu Val Gly
                                 100                 105                 110

Thr Lys Leu Asp Met Arg Asp Lys Glu Thr Gln Asp Arg Leu Lys Glu
                                 115                 120                 125

Lys Lys Leu Tyr Pro Ile Ser Tyr Glu Gln Gly Leu Ala Lys Met Lys
                         130                 135                 140

Glu Ile Asn Ala Val Lys Tyr Leu Glu Cys Ser Ala Leu Thr Glu Lys
         145                     150                 155                 160

Gly Leu Lys Thr Val Phe Asp Glu Ala Ile Arg Ala Val Ile Asn Pro
                                 165                 170                 175

Pro Leu Ser Lys Lys Lys Ser Ser Gly Gly Cys Asn Ile Leu
                         180                 185                 190

(2) INFORMATION FOR SEQ ID NO:29:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (A) ORGANISM: Dictyostelium discoideum (xi) SEQUENCE DESCRIPTION: SEQ ID NO:29:

Met Gln Ser Ile Lys Leu Val Val Gly Asp Gly Ala Val Gly Lys
         1                       5                   10                  15

Thr Cys Leu Leu Ile Ser Tyr Thr Ser Asn Ser Phe Pro Thr Glu Tyr
                         20                  25                  30

Val Pro Thr Val Phe Asp Asn Tyr Ser Ala Asn Val Met Val Asp Asn
                         35                  40                  45

Lys Thr Val Ser Leu Gly Leu Trp Asp Thr Ala Gly Gln Glu Asp Tyr
                         50                  55                  60

Asp Arg Leu Arg Pro Leu Ser Tyr Pro Gln Thr Asp Val Phe Leu Ile
         65                      70                  75                  80

Cys Phe Ala Ile Ile Ser Gln Ser Tyr Thr Asn Val Lys Ser Lys Trp
                                 85                  90                  95

Trp Pro Glu Val Thr His His Cys Pro Asn Cys Thr Ile Leu Val Gly
                                 100                 105                 110

Thr Lys Cys Asp Leu Arg Asp Lys Glu Ser Leu Glu Lys Leu Arg Glu
                                 115                 120                 125

Lys His Gln Gln Pro Leu Thr Phe Gln Gln Gly Glu Gln Met Ala Lys
                         130                 135                 140
```

```
    Glu Ile Lys Ala Phe Cys Tyr Met Glu Cys Ser Ala Leu Thr Gln Lys
    145                 150                 155                 160

Gly Leu Lys Gln Val Phe Asp Glu Ala Ile Lys Ala Val Ile Phe Pro
                    165                 170                 175

Asp Arg Asp Lys Ala Thr Asn Lys Lys Asn Ser Lys Cys Ser Ile Leu
                180                 185                 190
```

(2) INFORMATION FOR SEQ ID NO:30:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:30:

```
    Met Ser Ala Ala Glu Val Ile Lys Leu Val Val Ile Gly Gly Ala Val
    1               5                   10                  15

Gly Lys Thr Cys Leu Leu Ile Tyr Ala Asn Asn Arg Phe Pro Glu Asp
                    20                  25                  30

Tyr Ile Pro Thr Val Phe Asp Asn Tyr Val Val Asn Leu Thr Ala Gly
                35                  40                  45

Asp Arg Asn Ile Glu Leu Gly Leu Trp Asp Thr Ala Gly Glu Tyr Asp
    50                  55                  60

Lys Leu Arg Pro Leu Ser Tyr Ala Asn Asn Val Phe Leu Ile Cys Phe
    65                  70                  75                  80

Ser Ile Asn Pro Val Ser Phe Glu Asn Val Tyr Thr Lys Trp Tyr Pro
                    85                  90                  95

Glu Val Met His Phe Cys Pro Glu Val Gln Ile Leu Val Gly Thr Lys
                    100                 105                 110

Leu Asp Thr Arg Asp Asp Arg Gly Val Leu Asp Lys Leu Gln Gln Thr
                    115                 120                 125

Gly His Lys Pro Ile Thr Thr Glu Gln Gly Asn Asp Leu Ala Arg Arg
                130                 135                 140

Ile Lys Ala Ile Lys Tyr Met Glu Cys Ser Ala Lys Thr Ser Gln Asn
    145                 150                 155                 160

Leu Lys Gln Val Phe Asp Glu Ala Ile Lys Ser Val Leu Phe Ile Lys
                    165                 170                 175

Lys Lys Lys Ser Lys Cys Ile Val Met
                180                 185
```

(2) INFORMATION FOR SEQ ID NO:31:

(i) SEQUENCE CHARACTERISTICS:
        (A) LENGTH: 205 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:31:

Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
                20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
        50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                85                  90                  95

Glu Met Glu Ser Phe Ala Ala Thr Ala Asp Phe Arg Glu Gln Ile Leu
                100                 105                 110

Arg Val Lys Glu Asp Glu Asn Val Pro Phe Leu Leu Val Gly Asn Lys
            115                 120                 125

Ser Asp Leu Glu Asp Lys Arg Gln Val Ser Val Glu Glu Ala Lys Asn
        130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                165                 170                 175

Ala Arg Lys Met Glu Asp Ser Lys Lys Asn Gly Lys Lys Lys Arg Lys
                180                 185                 190

Ser Leu Ala Lys Arg Ile Arg Glu Arg Cys Cys Ile Leu
            195                 200                 205

(2) INFORMATION FOR SEQ ID NO:32:

(i) SEQUENCE CHARACTERISTICS:
       (A) LENGTH: 204 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Homo sapiens (xi) SEQUENCE DESCRIPTION: SEQ ID NO:32:

Met Ala Ala Asn Lys Ser Lys Gly Gln Ser Ser Leu Ala Leu His Lys
1               5                   10                  15

Val Ile Met Val Gly Ser Gly Gly Val Gly Lys Ser Ala Leu Thr Leu
                20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Ile Asp
        50                  55                  60

Ile Leu Asp Thr Ala Gly Gln Glu Asp Tyr Ala Ile Arg Asp Asn Tyr
65                  70                  75                  80

Phe Arg Ser Gly Glu Gly Phe Leu Leu Val Phe Ser Ile Thr Glu His
                85                  90                  95

Glu Ser Phe Thr Ala Thr Ala Glu Phe Arg Glu Gln Ile Leu Arg Val
            100                 105                 110

Lys Ala Glu Glu Asp Lys Ile Pro Leu Leu Val Val Gly Asn Lys Ser 115                 120                 125
    Asp Leu Glu Glu Arg Arg Gln Val Pro Val Glu Glu Ala Arg Ser Lys
        130                 135                 140

Ala Glu Glu Trp Gly Val Gln Tyr Val Glu Thr Ser Ala Lys Thr Arg
    145                 150                 155                 160

Ala Asn Val Asp Lys Val Phe Phe Asp Leu Met Arg Glu Ile Arg Thr
                        165                 170                 175

Lys Lys Met Ser Glu Asn Lys Asp Lys Asn Gly Lys Lys Ser Ser Lys
                    180                 185                 190

Asn Lys Lys Ser Phe Lys Glu Arg Cys Cys Leu Leu
                    195                 200

(2) INFORMATION FOR SEQ ID NO:33:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Discopyge ommata (xi) SEQUENCE DESCRIPTION: SEQ ID NO:33:

Met Ala Ala Asn Lys Asn Lys Asn Gln Ser Ser Leu Leu Lys Val Ile
    1               5                   10                  15

Met Val Gly Ser Gly Gly Val Gly Lys Ser Ala Leu Thr Leu Gln Phe
                    20                  25                  30

Met Tyr Asp Glu Phe Val Glu Asp Tyr Glu Pro Thr Lys Ala Asp Ser
                    35                  40                  45

Tyr Arg Lys Lys Val Val Leu Asp Gly Glu Val Gln Ile Asp Ile Leu
            50                  55                  60

Asp Thr Ala Gly Gln Glu Asp Tyr Ala Ile Arg Asp Asn Tyr Phe Arg
    65                  70                  75                  80

Ser Gly Glu Gly Phe Leu Cys Val Phe Ser Ile Glu Gln Glu Ser Phe
                        85                  90                  95

Thr Ala Thr Val Glu Phe Arg Glu Gln Ile Leu Arg Val Lys Glu Glu
                    100                 105                 110

Asp Lys Ile Pro Leu Leu Leu Val Gly Asn Lys Ser Asp Leu Glu Asp
                    115                 120                 125

Arg Arg Gln Val Ser Ile Glu Glu Ala Arg Ser Lys Ala Glu Glu Trp
            130                 135                 140

Gly Val Gln Tyr Val Glu Thr Ser Ala Lys Thr Arg Ala Asn Val Asp
    145                 150                 155                 160

Lys Val Phe Phe Asp Leu Met Arg Glu Val Arg Ala Lys Lys Met Ser
                        165                 170                 175

Glu Asn Lys Asp Lys Asn Gly Lys Lys Ser Ser Arg Asn Lys Lys Ser
                    180                 185                 190

Leu Arg Glu Arg Cys Cys Ile Leu
                    195                 200

(2) INFORMATION FOR SEQ ID NO:34:

(i) SEQUENCE CHARACTERISTICS:
        (A) LENGTH: 194 amino acids
        (B) TYPE: amino acid (C) STRANDEDNESS: single
(D) TOPOLOGY: linear (ii) MOLECULE TYPE: protein (iii) HYPOTHETICAL: NO (vi) ORIGINAL SOURCE:
    (A) ORGANISM: Discopyge ommata (xi) SEQUENCE DESCRIPTION: SEQ ID NO:34:

```
Met Ala Lys Lys Thr Tyr Asp Leu Leu Phe Lys Leu Leu Ile Gly
1               5                   10                  15

Asp Ser Gly Val Gly Lys Thr Cys Val Leu Phe Arg Phe Ser Asp Asp
                20                  25                  30

Ala Phe Asn Thr Thr Phe Ile Ser Thr Ile Gly Ile Asp Phe Lys Ile
        35                  40                  45

Lys Thr Val Glu Leu His Gly Lys Lys Ile Lys Leu Gln Ile Trp Asp
50                  55                  60

Thr Ala Gly Gln Glu Arg Phe His Thr Ile Thr Ser Tyr Tyr Arg Gly
65                  70                  75                  80

Ala Met Gly Ile Met Leu Val Tyr Asp Ile Thr Asn Ala Lys Ser Phe
                85                  90                  95

Glu Asn Ile Ser Lys Trp Leu Arg Asn Ile Asp Glu His Ala Asn Glu
                100                 105                 110

Asp Val Glu Arg Met Leu Leu Gly Asn Lys Asp Met Glu Asp Lys Arg
                115                 120                 125

Val Val Leu Lys Ser Lys Gly Gln Ile Ala Glu His Ala Ile Arg Phe
                130                 135                 140

Phe Glu Thr Ser Ala Lys Ala Asn Ile Asn Ile Glu Lys Ala Phe Leu
145                 150                 155                 160

Thr Leu Ala Glu Asp Ile Leu Gln Lys Thr Pro Val Lys Glu Pro Asp
                165                 170                 175

Arg Glu Asn Val Asp Ile Ser Thr Gly Gly Gly Leu Lys Lys Cys
                180                 185                 190

Cys Ser
```

(2) INFORMATION FOR SEQ ID NO:35:

(i) SEQUENCE CHARACTERISTICS:
    (A) LENGTH: 207 amino acids
    (B) TYPE: amino acid
    (C) STRANDEDNESS: single
    (D) TOPOLOGY: linear (ii) MOLECULE TYPE: protein (iii) HYPOTHETICAL: NO (vi) ORIGINAL SOURCE:
    (A) ORGANISM: Discopyge ommata (xi) SEQUENCE DESCRIPTION: SEQ ID NO:35:

```
Met Lys Thr Tyr Asp Tyr Leu Phe Lys Leu Leu Leu Ile Gly Asp Ser
1               5                   10                  15

Gly Val Gly Lys Thr Cys Leu Leu Phe Arg Phe Ser Glu Asp Ala Phe
                20                  25                  30

Asn Thr Thr Phe Ile Ser Thr Ile Gly Ile Asp Phe Lys Ile Arg Thr
            35                  40                  45

Val Glu Leu Asp Gly Lys Lys Ile Lys Leu Gln Ile Trp Asp Thr Ala
50                  55                  60
```

```
Gly Gln Glu Arg Phe Arg Thr Ile Thr Ala Tyr Tyr Arg Gly Ala Met
65                  70                  75                  80

Gly Ile Met Lys Val Asp Ile Thr Asn Glu Lys Ser Phe Asp Asn Ile
            85                  90                  95

Lys Asn Trp Ile Arg Asn Ile Glu Glu His Ala Ser Ser Asp Val Glu
            100                 105                 110

Arg Met Ile Leu Gly Asn Lys Cys Asp Met Asn Glu Lys Arg Gln Val
            115                 120                 125

Ser Lys Glu Arg Gly Glu Lys Leu Ala Ile Asp Tyr Gly Ile Lys Phe
130                 135                 140

Leu Glu Thr Ser Ala Lys Ser Ser Ile Asn Val Glu Glu Ala Phe Ile
145                 150                 155                 160

Thr Leu Ala Arg Asp Ile Met Thr Lys Leu Asn Lys Lys Met Asn Glu
            165                 170                 175

Asn Ser Leu Gln Glu Ala Val Asp Lys Leu Lys Ser Pro Pro Lys Lys
            180                 185                 190

Pro Ser Gln Lys Lys Lys Gln Leu Ser Phe Arg Cys Ser Leu Leu
            195                 200                 205
```

(2) INFORMATION FOR SEQ ID NO:36:

(i) SEQUENCE CHARACTERISTICS:
      (A) LENGTH: 213 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
       (A) ORGANISM: Discopyge ommata (xi) SEQUENCE DESCRIPTION: SEQ ID NO:36:

```
Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Glu Phe Asn Leu Glu Ser Lys Ser Thr Ile Gly Val Glu Phe Ala
            35                  40                  45

Thr Arg Ser Ile Gln Val Asp Gly Lys Thr Ile Lys Gln Ile Trp Asp
50                  55                  60

Thr Gly Gln Glu Arg Tyr Arg Ala Ile Thr Ser Ala Tyr Tyr Arg Gly
65                  70                  75                  80

Ala Val Gly Ala Leu Leu Val Tyr Asp Ile Ala Lys His Leu Thr Tyr
            85                  90                  95

Glu Asn Val Glu Arg Trp Leu Lys Glu Leu Arg Asp His Ala Asp Asn
            100                 105                 110

Asn Ile Val Ile Met Leu Val Gly Asn Lys Ser Asp Leu Arg His Leu
            115                 120                 125

Arg Val Pro Thr Asp Ala Arg Ala Phe Ala Glu Lys Asn Asn Leu Ser
130                 135                 140

Phe Ile Glu Thr Ser Ala Leu Asp Ser Thr Asn Val Glu Glu Ala Phe
145                 150                 155                 160

Lys Asn Ile Leu Thr Glu Ile Tyr Arg Ile Val Ser Gln Lys Gln Ile
            165                 170                 175

Ser Asp Arg Ser Ala His Asp Glu Ser Pro Gly Asn Asn Val Val Asp
            180                 185                 190
```

```
    Ile Ser Val Pro Pro Thr Thr Asp Gly Gln Lys Ser Asn Lys Leu Gln
            195                 200                 205

Cys Cys Gln Asn Met
            210
```

(2) INFORMATION FOR SEQ ID NO:37:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:37:

```
    Met Pro Leu Arg Phe Lys Ile Val Val Leu Gly Ser Gly Val Gly
    1               5                   10                  15

Lys Ser Ala Leu Thr Val Gln Phe Val Gln Gly Ile Phe Val Glu Lys
                    20                  25                  30

Tyr Asp Pro Thr Ile Glu Asp Ser Tyr Arg Lys Gln Val Glu Val Asp
                35                  40                  45

Ser Asn Gln Cys Met Leu Glu Ile Leu Asp Thr Ala Gly Thr Glu Gln
            50                  55                  60

Phe Thr Met Arg Asp Leu Tyr Met Lys Asn Gly Gln Gly Phe Val Leu
    65                  70                  75                  80

Val Tyr Ser Ile Ile Ser Asn Ser Thr Phe Asn Glu Leu Pro Asp Leu
                    85                  90                  95

Arg Glu Gln Ile Leu Arg Val Lys Asp Cys Glu Asp Val Pro Met Val
                100                 105                 110

Leu Val Gly Asn Lys Cys Asp Leu His Asp Gln Arg Val Ile Ser Thr
                115                 120                 125

Glu Gln Gly Glu Glu Leu Ala Arg Lys Phe Gly Asp Cys Tyr Phe Leu
            130                 135                 140

Glu Ala Ser Ala Lys Asn Lys Val Asn Val Glu Gln Ile Phe Tyr Asn
    145                 150                 155                 160

Leu Ile Arg Gln Ile Asn Arg Lys Asn Pro Val Gly Pro Pro Ser Lys
                    165                 170                 175

Ala Lys Ser Lys Cys Ala Leu Leu
                180
```

(2) INFORMATION FOR SEQ ID NO:38:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:38:

```
    Met Arg Glu Tyr Lys Val Val Val Leu Gly Ser Gly Gly Val Gly Lys
```

```
                1               5                    10                       15

Ser Ala Leu Thr Val Gln Phe Val Thr Gly Thr Phe Ile Glu Lys Tyr
                            20                   25                   30

Asp Pro Thr Ile Glu Asp Phe Tyr Arg Lys Glu Ile Glu Val Asp Ser
                            35                   40                   45

Ser Pro Ser Val Leu Glu Ile Leu Asp Thr Ala Gly Thr Glu Gln Phe
                            50                   55                   60

Ala Ser Arg Asp Leu Tyr Ile Lys Asn Gly Gln Gly Phe Ile Leu Val
           65                   70                   75                   80

Tyr Ser Leu Val Asn Gln Gln Phe Gln Asp Ile Lys Pro Met Arg Asp
                                 85                   90                   95

Gln Ile Ile Arg Val Lys Tyr Glu Lys Val Pro Val Ile Leu Val Gly
                           100                  105                  110

Asn Lys Val Asp Leu Glu Ser Glu Arg Glu Val Ser Ser Ser Glu Gly
                           115                  120                  125

Arg Ala Leu Ala Glu Glu Trp Gly Cys Pro Phe Met Glu Thr Ser Ala
                           130                  135                  140

Lys Ser Lys Thr Met Val Asp Glu Leu Phe Ala Glu Ile Val Arg Gln
           145                  150                  155                  160

Met Asn Tyr Ala Ala Gln Pro Asp Lys Asp Asp Pro Cys Cys Ser Ala
                                165                  170                  175

Cys Asn Gln (2) INFORMATION FOR SEQ ID NO:39:

(i) SEQUENCE CHARACTERISTICS:
           (A) LENGTH: 183 amino acids
           (B) TYPE: amino acid
           (C) STRANDEDNESS: single
           (D) TOPOLOGY: linear (ii) MOLECULE TYPE: protein (iii) HYPOTHETICAL: NO (vi) ORIGINAL SOURCE:
           (A) ORGANISM: Homo sapiens (xi) SEQUENCE DESCRIPTION: SEQ ID NO:39:

Met Arg Glu Tyr Lys Val Val Leu Gly Ser Gly Gly Val Gly Lys
           1                5                   10                   15

Ser Ala Leu Thr Val Gln Phe Val Thr Gly Ser Phe Ile Glu Lys Tyr
                            20                   25                   30

Asp Pro Thr Ile Glu Asp Phe Tyr Arg Lys Glu Ile Glu Val Asp Ser
                            35                   40                   45

Ser Pro Ser Val Leu Glu Ile Leu Asp Thr Ala Gly Thr Glu Gln Phe
                            50                   55                   60

Ala Ser Met Arg Asp Leu Tyr Ile Lys Asn Gly Gln Gly Phe Ile Leu
           65                   70                   75                   80

Val Tyr Ser Leu Val Asn Gln Gln Ser Phe Gln Asp Ile Lys Pro Met
                                 85                   90                   95

Arg Asp Gln Ile Ile Arg Val Lys Arg Tyr Glu Arg Val Pro Met Ile
                           100                  105                  110

Leu Val Gly Asn Lys Val Asp Leu Glu Gly Glu Arg Glu Val Ser Tyr
                           115                  120                  125

Gly Glu Gly Lys Ala Leu Ala Glu Glu Trp Ser Cys Pro Phe Met Glu
                           130                  135                  140

Thr Ser Ala Lys Asn Lys Ala Ser Val Asp Glu Leu Phe Ala Glu Ile
```

```
                145                 150                 155                 160
        Val Arg Gln Met Asn Tyr Ala Ala Gln Ser Asn Gly Asp Glu Gly Cys
                        165                 170                 175

Cys Ser Ala Cys Val Ile Leu
                        180
```

(2) INFORMATION FOR SEQ ID NO:40:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Discopyge ommata (xi) SEQUENCE DESCRIPTION: SEQ ID NO:40:

```
        Met Arg Glu Tyr Lys Leu Val Val Leu Gly Ser Gly Gly Val Gly Lys
        1               5                   10                  15

Ser Ala Leu Thr Val Gln Phe Val Gln Gly Ile Phe Val Glu Lys Tyr
                        20                  25                  30

Asp Pro Thr Ile Glu Asp Ser Tyr Arg Lys Gln Val Glu Val Asp Cys
                        35                  40                  45

Gln Pro Cys Met Leu Glu Ile Leu Asp Thr Ala Gly Thr Glu Gln Phe
                50                  55                  60

Thr Ala Met Arg Asp Leu Tyr Met Lys Asn Gly Gln Gly Phe Ala Leu
        65                      70                  75                  80

Val Tyr Ser Ile Thr Ala Gln Ser Thr Phe Asn Asp Leu Gln Asp Leu
                        85                  90                  95

Arg Glu Gln Ile Leu Arg Val Lys Asp Thr Glu Asp Val Pro Met Ile
                        100                 105                 110

Leu Val Gly Asn Lys Cys Asp Leu Glu Asp Glu Arg Val Val Gly Lys
                        115                 120                 125

Glu Gln Gly Gln Asn Leu Ala Arg Gln Trp Asn Asn Cys Ala Phe Leu
                        130                 135                 140

Glu Ser Ser Ala Lys Ser Lys Ile Asn Val Asn Glu Ile Phe Tyr Asp
        145                     150                 155                 160

Leu Val Arg Gln Ile Asn Arg Lys Ala Pro Val Glu Lys Cys Lys Lys
                        165                 170                 175

Lys Lys Ser Gln Cys Thr Leu Leu
                        180
```

(2) INFORMATION FOR SEQ ID NO:41:

(i) SEQUENCE CHARACTERISTICS:
        (A) LENGTH: 180 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:41:

```
Met Arg Glu Tyr Lys Leu Val Val Gly Ser Gly Gly Val Gly Lys Ser
1               5                   10                  15

Ala Leu Thr Val Gln Phe Val Gln Gly Phe Val Glu Lys Tyr Asp Pro
            20                  25                  30

Thr Ile Glu Asp Ser Tyr Arg Lys Gln Val Glu Val Asp Cys Gln Gln
        35                  40                  45

Cys Met Leu Glu Asp Thr Ala Gly Thr Glu Gln Phe Thr Ala Met Arg
50                  55                  60

Asp Leu Tyr Met Lys Asn Gly Gln Gly Phe Ala Leu Val Tyr Ser Ile
65                  70                  75                  80

Thr Ala Gln Ser Thr Phe Asn Asp Leu Gln Asp Leu Arg Glu Gln Ile
                85                  90                  95

Leu Arg Val Lys Asp Thr Glu Asp Val Pro Met Ile Leu Val Gly Asn
            100                 105                 110

Lys Cys Asp Leu Glu Asp Glu Arg Val Val Gly Lys Glu Gln Gly Gln
            115                 120                 125

Asn Leu Ala Arg Gln Trp Cys Asn Cys Ala Phe Leu Glu Ser Ser Ala
            130                 135                 140

Lys Ser Lys Ile Asn Val Asn Glu Ile Phe Tyr Asp Leu Val Arg Gln
145                 150                 155                 160

Ile Asn Arg Lys Thr Pro Val Glu Lys Lys Lys Pro Lys Lys Lys Ser
                165                 170                 175

Cys Leu Leu Leu
            180

(2) INFORMATION FOR SEQ ID NO:42:

(i) SEQUENCE CHARACTERISTICS:
        (A) LENGTH: 179 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:42:

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
                20                  25                  30

Asp Pro Thr Ile Glu Asp Ser Tyr Arg Lys Gln Val Glu Val Asp Ala
            35                  40                  45

Gln Gln Cys Met Leu Glu Ile Leu Asp Thr Ala Gly Thr Glu Gln Phe
50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Val Pro Met Ile
            100                 105                 110

Leu Val Gly Asn Lys Cys Asp Leu Glu Asp Glu Arg Val Val Gly Lys
            115                 120                 125

Glu Gln Gly Gln Asn Leu Ala Arg Gln Trp Asn Asn Cys Ala Phe Leu
130                 135                 140
```

Glu Ser Ser Ala Lys Ser Lys Ile Asn Val Glu Ile Phe Tyr Asp Leu
145                 150                 155                 160

Val Arg Gln Ile Asn Arg Lys Thr Pro Val Pro Gly Lys Ala Arg Lys
                165                 170                 175

Lys Ser Ser (2) INFORMATION FOR SEQ ID NO:43:

(i) SEQUENCE CHARACTERISTICS:
       (A) LENGTH: 184 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Drosophila melanogaster (xi) SEQUENCE DESCRIPTION: SEQ ID NO:43:

Met Arg Glu Tyr Lys Ile Val Val Leu Gly Ser Gly Gly Val Gly Lys
1               5                   10                  15

Ser Ala Leu Thr Val Gln Phe Val Gln Cys Ile Phe Val Glu Lys Tyr
                20                  25                  30

Asp Pro Thr Ile Glu Asp Ser Tyr Arg Lys Gln Val Glu Val Asp Gly
                35                  40                  45

Gln Gln Cys Met Leu Glu Ile Leu Asp Thr Ala Gly Thr Glu Gln Phe
        50                  55                  60

Thr Ala Met Arg Asp Leu Tyr Met Lys Asn Gly Gln Gly Phe Val Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Val
                100                 105                 110

Leu Val Gly Asn Lys Cys Asp Leu Glu Glu Glu Arg Val Val Gly Lys
            115                 120                 125

Glu Leu Gly Lys Asn Leu Ala Thr Gln Phe Asn Cys Ala Phe Met Glu
130                 135                 140

Thr Ser Ala Lys Ala Lys Val Asn Val Asn Asp Ile Phe Tyr Asp Leu
145                 150                 155                 160

Val Arg Gln Ile Asn Lys Lys Ser Pro Glu Lys Lys Gln Lys Lys Pro
                165                 170                 175

Lys Lys Ser Leu Cys Val Leu Leu
            180

(2) INFORMATION FOR SEQ ID NO:44:

(i) SEQUENCE CHARACTERISTICS:
       (A) LENGTH: 182 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Dictyostelium discoideum (xi) SEQUENCE DESCRIPTION: SEQ ID NO:44:

Met Thr Glu Tyr Lys Leu Val Ile Val Gly Gly Gly Val Gly Lys
1               5                   10                  15

Ser Leu Thr Ile Gln Leu Ile Gln Asn His Phe Asp Glu Tyr Asp Pro
            20                  25                  30

Thr Ile Glu Asp Ser Tyr Arg Lys Gln Val Ser Ile Asp Asp Glu Thr
                35                  40                  45

Cys Leu Leu Ile Leu Asp Thr Ala Gly Gln Glu Ser Ala Met Arg
50                  55                  60

Asp Gln Tyr Met Arg Thr Gly Gln Gly Phe Leu Cys Val Tyr Ser Ile
65                  70                  75                  80

Thr Ser Arg Ser Ser Tyr Asp Glu Ile Ala Ser Phe Arg Glu Gln Ile
                85                  90                  95

Leu Arg Val Lys Asp Lys Asp Arg Val Pro Leu Ile Leu Val Gly Asn
                100                 105                 110

Lys Ala Asp Leu Asp His Glu Arg Gln Val Ser Val Asn Glu Gly Gln
                115                 120                 125

Glu Leu Ala Lys Asp Ser Leu Ser Phe His Glu Ser Ser Ala Lys Ser
130                 135                 140

Arg Ile Asn Val Glu Glu Ala Phe Tyr Ser Leu Val Arg Glu Ile Arg
145                 150                 155                 160

Lys Glu Leu Lys Gly Asp Gln Ser Ser Gly Lys Ala Gln Lys Lys Lys
                165                 170                 175

Lys Gln Cys Leu Ile Leu
                180

(2) INFORMATION FOR SEQ ID NO:45:

(i) SEQUENCE CHARACTERISTICS:
       (A) LENGTH: 190 amino acids
       (B) TYPE: amino acid
       (C) STRANDEDNESS: single
       (D) TOPOLOGY: linear (ii) MOLECULE TYPE: protein (iii) HYPOTHETICAL: NO (vi) ORIGINAL SOURCE:
       (A) ORGANISM: Dictyostelium discoideum (xi) SEQUENCE DESCRIPTION: SEQ ID NO:45:

Met Ser Val Ser Asn Glu Tyr Lys Leu Val Val Gly Gly Gly Val
1               5                   10                  15

Gly Lys Ser Ala Leu Thr Ile Gln Phe Gln Asn His Phe Ile Glu Glu
                20                  25                  30

Tyr Asp Pro Thr Ile Glu Asp Ser Tyr Arg Arg Gln Cys Gln Val Asp
                35                  40                  45

Glu Asp Thr Cys Leu Leu Asp Ile Leu Asp Thr Ala Gly Gln Asp Asp
        50                  55                  60

Tyr Ser Met Arg Asp Gln Tyr Met Arg Thr Gly Gln Gly Phe Leu Val
65                  70                  75                  80

Tyr Asp Val Ser Arg Thr Ser Phe Glu Glu Ile Asn Val Val Glu Gln
                85                  90                  95

Ile Arg Val Lys Asp Asn Asp Lys Val Pro Ile Val Leu Val Gly Asn
                100                 105                 110

Lys Cys Asp Leu Glu Asn Leu Arg Glu Val Thr Glu Gly Glu Gly Ser
                115                 120                 125

Glu Leu Ala Lys Ser Phe Ser Val Pro Phe Leu Glu Thr Ser Ala Lys

```
                    130           135           140
    Lys Arg Leu Asn Val Asp Glu Cys Phe Phe Glu Val Val Arg Glu Ile
    145                 150                 155                 160

Lys Lys Ser Leu Lys Glu Pro Gly Arg Ser Lys Lys Asp Lys Lys Gly
                    165                 170                 175

Gly Ile Leu Lys Lys Phe Lys Gly Gly Asp Cys Leu Ile Leu
                    180                 185                 190
```

(2) INFORMATION FOR SEQ ID NO:46:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:46:

```
    Met Ser Lys Leu Leu Lys Leu Val Ile Val Gly Asp Gly Gly Val Gly
    1               5                   10                  15

Lys Ser Ala Leu Thr Ile Gln Leu Thr Gln Asn Gln Phe Ile Ala Glu
                    20                  25                  30

Tyr Asp Pro Thr Ile Glu Asn Ser Tyr Arg Lys Gln Val Asn Ile Asp
                35                  40                  45

Glu Glu Val Tyr Met Leu Asp Ile Leu Asp Thr Ala Gly Gln Glu Glu
    50                  55                  60

Tyr Ser Ala Met Arg Asp Gln Tyr Ile Arg Ser Gly Arg Gly Phe Leu
    65                  70                  75                  80

Ile Val Tyr Ser Ile Ile Ser Arg Ala Ser Phe Glu Ala Val Thr Thr
                    85                  90                  95

Phe Arg Glu Gln Ile Leu Arg Val Lys Asp Leu Ser Thr Tyr Pro Ile
                    100                 105                 110

Val Ile Ile Gly Asn Lys Ala Asp Leu Pro Asp Lys Asp Arg Lys Val
                    115                 120                 125

Pro Pro Met Glu Gly Lys Glu Leu Ala Lys Phe Gly Ala Pro Phe Leu
            130                 135                 140

Glu Thr Ser Ala Lys Ser Arg Val Asn Val Glu Ala Phe Phe Thr
    145                 150                 155                 160

Leu Val Arg Glu Ile Lys Arg Trp Asn Gln Asn Pro Gln Asn Glu Glu
                    165                 170                 175

Met Leu Pro Pro Lys Lys Arg Gly Cys Ile Ile Leu
                    180                 185
```

(2) INFORMATION FOR SEQ ID NO:47:

(i) SEQUENCE CHARACTERISTICS:
        (A) LENGTH: 188 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Dictyostelium discoideum (xi) SEQUENCE DESCRIPTION: SEQ ID NO:47:

```
Met Glu Tyr Lys Leu Val Ile Val Gly Gly Gly Val Gly Lys Ser
1               5                   10                  15

Ala Leu Thr Ile Gln Leu Ile Gln Asn His Phe Ile Asp Glu Tyr Asp
            20                  25                  30

Pro Thr Ile Glu Asp Ser Tyr Arg Lys Gln Val Thr Ile Asp Glu Glu
            35                  40                  45

Thr Cys Leu Leu Asp Ile Leu Asp Thr Ala Gly Gln Glu Glu Tyr Ser
50                  55                  60

Ala Met Arg Asp Gln Tyr Met Arg Thr Gly Gln Gly Phe Leu Cys Val
65                  70                  75                  80

Tyr Ser Ile Thr Ser Arg Ser Ser Phe Asp Glu Ile Ala Ser Phe Arg
            85                  90                  95

Glu Gln Ile Leu Arg Val Lys Asp Lys Asp Arg Val Pro Met Ile Val
            100                 105                 110

Val Gly Asn Lys Cys Asp Leu Glu Ser Asp Arg Gln Val Thr Thr Gly
            115                 120                 125

Glu Gly Gln Asp Leu Ala Lys Ser Phe Gly Ser Pro Phe Leu Glu Thr
            130                 135                 140

Ser Ala Lys Ile Arg Val Asn Val Glu Glu Ala Phe Tyr Ser Leu Val
145                 150                 155                 160

Arg Glu Ile Arg Lys Asp Leu Lys Gly Asp Ser Lys Pro Glu Lys Gly
            165                 170                 175

Lys Lys Lys Arg Pro Leu Lys Ala Cys Thr Leu Leu
            180                 185
```

(2) INFORMATION FOR SEQ ID NO:48:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Caenorhabditis elegans (xi) SEQUENCE DESCRIPTION: SEQ ID NO:48:

```
Met Ser Ser Ser Leu Gln Ser Asn Arg Gln Ser Leu Asn Arg Lys Val
1               5                   10                  15

Ala Val Met Gly Tyr Pro His Val Gly Lys Ser Ala Leu Val Leu Arg
            20                  25                  30

Phe Thr Gln Asn Ile Phe Pro Glu Arg Tyr Glu Ser Thr Ile Glu Asp
            35                  40                  45

Gln His Ser Lys His Ile Ala Ala Phe His Arg Asp Tyr His Leu Arg
50                  55                  60

Val Thr Asp Thr Ala Gly Gln Gln Glu Tyr Thr Val Phe Pro Arg Ser
65                  70                  75                  80

Cys Ser Leu Asp Ile Asn Gly Phe Ile Leu Val Tyr Ala Ile Asp Asp
            85                  90                  95

Arg Lys Ser Phe Glu Met Cys Ser Asn Ile Tyr Glu Lys Ile Val Arg
            100                 105                 110

Thr Tyr Gly Asp Thr Ser Ile Pro Ile Val Ile Val Gly Lys Thr Asp
            115                 120                 125
```

```
Leu Ser Thr Gln Val Val Arg Ala Glu Gly Glu Leu Ala Arg
    130                 135             140

Gln Trp Asp Ala Lys Phe Val Glu Ile Thr Ala Arg Glu Ser Asn Arg
145                 150                 155                 160

Val His Glu Val Phe Glu Leu Leu Arg Glu Ile Glu Ile Ser Arg
                165                 170                 175

Gly Asn Leu Ser Pro Thr Glu Arg Pro Asn Gly Asn Ser Pro Lys Arg
                180                 185                 190

Pro Phe Lys Asp Asp Gly Lys Pro Cys Ser Ile Ser
            195                 200
```

(2) INFORMATION FOR SEQ ID NO:49:

(i) SEQUENCE CHARACTERISTICS:
      (A) LENGTH: 215 amino acids
      (B) TYPE: amino acid
      (C) STRANDEDNESS: single
      (D) TOPOLOGY: linear (ii) MOLECULE TYPE: protein (iii) HYPOTHETICAL: NO (vi) ORIGINAL SOURCE:
      (A) ORGANISM: Coprinus cinereus (xi) SEQUENCE DESCRIPTION: SEQ ID NO:49:

```
Met Ala Ala Arg Ala Gln Phe Leu Arg Glu Tyr Lys Leu Val Val Val
1               5                   10                  15

Gly Gly Gly Gly Val Gly Lys Ser Ala Leu Thr Ile Gln Phe Ile Gln
                20                  25                  30

Ser His Phe Val Asp Glu Tyr Asp Pro Thr Ile Glu Asp Ser Tyr Arg
                35                  40                  45

Lys Gln Cys Ile Ile Asp Asp Glu Val Ala Leu Leu Asp Val Leu Asp
50                  55                  60

Thr Ala Gly Gln Glu Glu Tyr Gly Ala Met Arg Glu Gln Tyr Met Arg
65                  70                  75                  80

Thr Gly Glu Gly Phe Leu Leu Val Tyr Ser Ile Thr Ser Arg Asn Ser
                85                  90                  95

Phe Glu Glu Ile Ser Ile Phe His Gln Gln Ile Leu Arg Val Lys Asp
                100                 105                 110

Gln Asp Ser Phe Pro Val Ile Val Val Ala Asn Lys Cys Asp Leu Glu
                115                 120                 125

Tyr Glu Arg Gln Val Gly Met Asn Glu Gly Arg Asp Leu Ala Lys His
                130                 135                 140

Phe Gly Cys Lys Phe Ile Glu Thr Ser Ala Lys Gln Arg Ile Asn Val
145                 150                 155                 160

Asp Glu Ala Phe Ser Asn Leu Val Arg Glu Ile Arg Lys Tyr Asn Arg
                165                 170                 175

Glu Gln Gln Thr Gly Arg Pro Ala Ile Ala Ala Gly Gly Gly Gly Pro
                180                 185                 190

Ala Gly Ser Tyr Thr Gln Asp Arg His His Asp Glu Ala Pro Gly Cys
                195                 200                 205

Cys Ala Gly Cys Val Ile Ala
            210                 215
```

(2) INFORMATION FOR SEQ ID NO:50:

(i) SEQUENCE CHARACTERISTICS:

(A) LENGTH: 206 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Geodia cydonium (xi) SEQUENCE DESCRIPTION: SEQ ID NO:50:

Met Thr Glu Tyr Lys Ile Val Gly Gly Leu Val Gly Lys Ser
  1               5                  10                  15

Ala Leu Thr Leu Gln Leu Val Gln Val Cys Ile Lys Asp Gln Tyr Tyr
                 20                  25                  30

Leu Ile Glu Phe Gln Asn Asn Gln Phe Gln Phe Glu Asn Leu Gln Asn
                 35                  40                  45

His Tyr Ile Asp Tyr Asp Pro Thr Val Glu Asp Ser Arg Arg Glu Val
  50                  55                  60

Ser Ile Asp Asp Gln Thr Cys Leu Asn Ile Leu Asp Thr Ala Gly Gln
  65                  70                  75                  80

Gln His Ser Asn Ala Gln Ser Met Asp Ala His Trp Ser Thr Val Phe
                 85                  90                  95

Val Cys Leu Phe Asn Tyr Phe Asn Ile Thr Ser Met Tyr Asp Glu Ile
                 100                 105                 110

Ala Ser Phe Arg Glu Gln Ile Leu Arg Val Lys Asp Gly Ala Lys Asp
                 115                 120                 125

Leu Val Pro Leu Ile Leu Ile Ile Asn Lys Ala Asp Leu Asp His Glu
                 130                 135                 140

Ser Gln Gly Ser Gly Asn Glu Gly Gln Leu Ala Lys Asp Ser Leu Ser
  145                 150                 155                 160

Phe His Gln Ser Ser Ala Lys Ser Arg Ile Asn Leu Glu Glu Ile Pro
                 165                 170                 175

Tyr Ser Leu Val Arg Glu Leu Arg Lys Glu Leu Lys Leu Asp Gln Ser
                 180                 185                 190

Ser Gly Lys Ala Gln Lys Lys Lys Gln Cys Leu Ile Ile
                 195                 200                 205

(2) INFORMATION FOR SEQ ID NO:51:

(i) SEQUENCE CHARACTERISTICS:
        (A) LENGTH: 198 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Canis familiaris (xi) SEQUENCE DESCRIPTION: SEQ ID NO:51:

Met Lys Lys Thr Tyr Asp Leu Leu Phe Lys Leu Leu Leu Ile Gly Asp
  1               5                  10                  15

Ser Gly Val Gly Lys Thr Cys Val Leu Phe Arg Phe Ser Asp Asp Ala
                 20                  25                  30

Phe Asn Thr Thr Phe Ile Ser Ile Gly Ile Asp Phe Lys Ile Lys Thr
                 35                  40                  45

```
         Val Glu Leu Gln Gly Lys Lys Ile Lys Leu Gln Ile Trp Asp Thr Ala
             50                  55                  60

Gly Gln Glu Arg Phe His Thr Ile Thr Thr Ser Tyr Tyr Arg Gly Ala
         65                  70                  75                  80

Met Gly Ile Met Leu Val Tyr Asp Ile Thr Asn Gly Lys Ser Phe Glu
                         85                  90                  95

Asn Ile Ser Lys Trp Leu Arg Asn Ile Asp Glu His Ala Asn Glu Asp
                        100                 105                 110

Val Glu Arg Met Leu Leu Gly Asn Lys Cys Asp Met Asp Asp Lys Arg
                    115                 120                 125

Val Val Pro Lys Gly Lys Gly Glu Gln Ile Ala Arg Glu His Gly Ile
                130                 135                 140

Arg Phe Phe Glu Thr Ser Ala Lys Val Asn Ile Asn Ile Glu Lys Ala
         145                 150                 155                 160

Phe Leu Thr Leu Ala Glu Asp Ile Leu Arg Lys Thr Pro Val Lys Glu
                         165                 170                 175

Pro Asn Ser Glu Asn Val Asp Ile Ser Ser Gly Gly Gly Val Thr Gly
                        180                 185                 190

Trp Lys Ser Lys Cys Cys
                        195
```

(2) INFORMATION FOR SEQ ID NO:52:

(i) SEQUENCE CHARACTERISTICS:
        (A) LENGTH: 214 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO:52:

```
         Met Gly Thr Arg Asp Asp Glu Tyr Asp Tyr Leu Phe Lys Val Val Leu
         1               5                   10                  15

Ile Gly Asp Ser Gly Val Gly Lys Ser Asn Leu Leu Ser Arg Phe Thr
                         20                  25                  30

Arg Asn Glu Phe Asn Leu Glu Ser Lys Ser Thr Ile Gly Val Glu Phe
                     35                  40                  45

Ala Thr Arg Ser Ile Gln Val Asp Gly Lys Thr Ile Lys Ala Gln Ile
             50                  55                  60

Trp Asp Thr Ala Gly Gln Glu Arg Tyr Arg Ala Ile Thr Ser Ala Tyr
         65                  70                  75                  80

Tyr Arg Gly Ala Val Gly Ala Leu Leu Val Tyr Asp Ile Ala Lys His
                         85                  90                  95

Leu Thr Tyr Glu Asn Val Glu Arg Trp Leu Lys Glu Leu Arg Asp His
                     100                 105                 110

Ala Asp Ser Asn Ile Val Ile Met Leu Val Gly Asn Lys Ser Asp Leu
                 115                 120                 125

Arg His Leu Arg Ala Val Pro Thr Asp Glu Ala Arg Ala Phe Ala Glu
                 130                 135                 140

Lys Asn Gly Leu Ser Phe Ile Glu Thr Ser Ala Leu Asp Ser Thr Asn
         145                 150                 155                 160

Val Glu Ala Ala Phe Gln Thr Ile Leu Thr Glu Ile Tyr Arg Ile Val
                         165                 170                 175
```

```
Ser Gln Lys Gln Met Ser Asp Arg Glu Asn Asp Met Ser Pro Ser Asn
        180                 185                 190

Asn Val Val Pro Ile His Val Pro Pro Thr Thr Glu Lys Pro Lys Val
        195             200                 205

Gln Cys Cys Gln Asn Ile
        210
```

PEPTIDOMIMETICS INHIBITING THE ONCOGENIC ACTION OF P21 RAS

This application is a Continuation-in-Part of U.S. Provisional Patent Application 60/004,091, filed Sep. 21, 1995.

FIELD OF THE INVENTION

This invention relates to peptidomimetic compounds effective in inhibiting oncogenesis, particularly as related to inhibition of p21 ras and adenocarcinomas of the colon, pancreatic carcinomas, neuroblastomas, and other cancers which express the transformed sequence of the ras gene product.

BACKGROUND OF THE INVENTION ras protooncogenes are activated by characteristic point mutations in a wide variety of malignancies. The expressed p21 ras proteins are oncogenic by virtue of single substituted amino acids, usually at position 12 or 61 of the 189-residue p21 ras gene product. ras proteins act as membrane-associated molecular switches that bind GTP and GDP and slowly hydrolyze GTP to GDP.

Mutations in ras are associated with the vast majority of adenocarcinomas of the colon. Cancer of the colon is a highly treatable and often curable disease when it remains localized to the bowel. It is the second most frequently diagnosed malignancy in the United States as well as the second most common cause of cancer death. Surgery is the primary treatment and results in cure in approximately 50% of patients. Adenocarcinoma is the primary lesion in the majority of cases. Recurrence following surgery is a major problem and often is the ultimate cause of death. The prognosis for colon cancer patients is clearly related to the degree of penetration of the tumor through the bowel wall and the presence or absence of nodal involvement. For locally advanced disease, the role of radiation therapy in colon cancer is under clinical evaluation. There is no standard therapy for advanced colon cancer and no evidence that chemotherapy improves survival, although short-term palliation may be achieved in approximately 10–20% of patients.

Pancreatic carcinoma has a high incidence of K-ras mutations. Mutated K-ras sequences which can be identified by polymerase chain reaction utilizing allele-specific primers can even be found in the plasma or serum from patients with pancreatic carcinoma. The c-Ki-ras oncogene is activated by point mutations involving codon 12 in 72%–100% of primary pancreatic adenocarcinomas, but the gene is not activated in nonneoplastic tissues. Cancer of the exocrine pancreas is rarely curable. The highest cure rate (4%–12%) occurs if the tumor is truly localized to the pancreas. Unfortunately, this stage of disease accounts for fewer than 20% of cases and, even with surgical resection, results in little more than a 5% 5-year survival rate. For small cancers (less than 2 cm) in the head of the pancreas with no lymph node metastases and no extension beyond the "capsule" of the pancreas, the survival rate following resection of the head of the pancreas approaches 20%. Overall survival rate of all stages is less than 2% at 5 years with most patients dying within one year. Worldwide, very few patients with cancers of the pancreatic tail or uncinate process have been cured.

Lung cancers also frequently involve ras mutations. Point mutations in codon 12 of the K-ras protooncogene occur more frequently in lung adenocarcinomas from smokers (30%) than they do in lung adenocarcinomas from nonsmokers (7%), suggesting that smoking is an important factor in the induction of these mutations. The ras oncogene may thus be a specific target of the mutagenic activity of tobacco smoke, and suggest that DNA alterations at this site can occur early and irreversibly during the development of adenocarcinomas of the lung.

Mutations in the ras protooncogenes are the most frequently observed molecular alteration in acute myeloid leukemia (AML). Whether ras mutations occur as late or relatively early events in the multistep process of myeloid transformation, remains an open question. There is significant evidence that the ras oncogene plays a role in experimental mammary carcinogenesis; the evidence in human breast cancer, however, is more limited.

Similarly, there is significant evidence that the ras oncogene plays a role in nitrosoamine-induced esophageal tumors in rats, but in human esophageal cancers ras gene mutations are more rarely found. However, it is probable that there is a significant role of mutated ras genes in both cell proliferation and malignant transformation of human esophageal cells.

Certain human neuroblastomas also show a high incidence of oncogenic ras mutations. Indeed, one study suggested that expressions of the oncogene N-myc and p21 together as detected by immunohistochemical staining could be among the most reliable prognostic indicators in neuroblastoma patients.

The ras proteins are key regulators of the growth of eukaryotic cells. Some of the direct targets are unknown. These target proteins include raf-1, gap, phosphatidylinositol-3-hydroxykinase and, very recently, two nuclear proteins, C-JUN and its kinase (JNK) The three-dimensional x-ray crystal structure for a ras-related protein bound to a domain of raf-1 has been elucidated. The ras-related protein (rak-1-a) binds to raf directly, utilizing residues contained in a sequence involving amino acids 35–37. All of the contact residues in the ras-related protein are homologous to those in the corresponding segment of ras-p-21. One of the inventors has shown that the p-21 ras protein (35–47 segment) selectively inhibits the mitogenic effects of oncogenic ras-p-21.

In addition to its role as an oncogene, the activation of ras proteins is a key step in the signal transduction pathways triggered by ligand-bound cell surface receptors, such as the insulin receptor.

The classical target of the ras protein is the GTPase activating protein GAP. This target protein is thought to play an essential role in the regulation of ras activity by increasing the GTPase activity of wild type, but not transformed ras. On the other hand, there is a considerable superfamily of these GAP-related proteins, which includes p120-GAP. Other target proteins besides mammalian gap itself include (1) IRA1 and IRA2, the functional equivalents of GAP in yeast. They regulate the ras-cyclic AMP pathway, controlling cell growth; (2) sar1, the fission yeast protein that regulates ras1 in that organism; (3) BUD2, a yeast protein that activates BUD1/RSR1 which participates in the regulation of bud-site selection; (4) Human neurofibromitosis (gene NF1). NF1 is associated with type 1 neurofibromatosis, one of the most frequently inherited genetic diseases characterized, in part, by multiple neural tumors. NF1 has been shown genetically and biochemically to interact with and stimulate the GTPase activity of ras; (5) Drosophila Gap1, which acts as a negative regulator of signalling by the Sevenless (SOS) receptor tyrosine kinase involved in eye development. Human SOS1 and SOS2 genes have also been recently identified which encode proteins that control GDP→GTP exchange on ras proteins and are involved in signal transduction by tyrosine kinase receptors. In situ hybridization shows that SOS1 maps to 2p22→p16 and SOS2 to 14q21→q22 in the human genome.

Another important target of ras is raf. The protein encoded by the c-raf-1 protooncogene is thought to function downstream of p21 ras because disruption of raf blocks signalling by ras in a number of systems. A highly-conserved 81 residue region of the N-terminus of raf protein has been shown to be critical as the ras protein interaction region. Importantly, the raf gene product interacts with both wild-type and activated ras protein. In one study, approximately 50% of the clones identified as interacting with ras were encoded portions of the c-raf and A-raf serine/threonine kinases. Thus, ras and the N-terminal region of raf protein associate directly in vitro and this interaction is dependent on GTP bound to ras.

Within the superfamily of ras-related GTP-binding proteins, only the ras protein itself has been shown to act as an oncogenic protein. Many other proteins, however, have substantial amino acid homology to ras. This ras superfamily of GTP-binding proteins (>50 members) regulates a diverse spectrum of intracellular processes. These include cellular proliferation and differentiation, intracellular vesicular trafficking, cytoskeletal control, NADPH oxidase function, as well as others. Some of these homologs may have biological activities which are related to ras. For example, rhoA encodes a ras-related GTP-binding protein that was thought principally to play a role in cytoskeletal organization. Recent evidence, however, has suggested both that rhoA could act either as a dominant oncogene, since transfection of both normal and activated rho genes confer a transformed phenotype on fibroblast cells in culture, or as a recessive tumor suppressor gene, by virtue, in part, of its chromosomal location at 3p21, a site deleted in many human malignancies. Thus, it is important to consider these ras homologs as potentially involved in cell growth and transformation.

Azatyrosine strongly inhibits oncogenic ras-p-21. This small molecule induces the rrg gene, which encodes a proteinase sequence showing 90% amino acid sequence identity to lysyl oxidase.

To acquire transforming potential, the precursor of the ras oncoprotein must undergo farnesylation or similar modification of the cysteine residue located in a carboxyl-terminal tetrapeptide. These C-terminal lipid modifications are essential for the interaction of ras-related proteins with membranes. While all ras proteins are farnesylated and some palmitoylated, the majority of other ras-related proteins are geranylgeranylated. Thus selective peptide and peptidomimetic inhibitors of ras lipidation have found potential utility as anti-oncogenic agents.

In view of the foregoing, there is a longfelt need in the art for agents which inhibit the transforming ability of ras. As described above, selective peptide and peptidomimetic inhibitors or ras lipidation have found potential utility as anti-oncogenic agents (Kohl et al. (1993) Science 260:1934–1937; James et al. (1993) Science 260:1937–1942). Similarly, FR patents 2694296 and 2690162 teach that peptides derived from the GAP protein may serve to inhibit ras. However, neither '694296 nor '690162 describes peptides derived from the ras protein itself. EP 203587 describes new ras oncogene polypeptides which are used for producing antibodies for immunogenic assays. However, these sequences are derived from ras and its homologs in the carboxyl terminal domain (residues 170–189 in SEQ ID NO:5) and are thus physically distant from and completely unrelated to any sequences claimed herein. Furthermore, these sequences were claimed for the production of antibodies, preferably by linking to an immunogenic carrier, and a claim for direct therapeutic application was not made.

Thus, peptides constructed from ras and its homologs for therapeutic application, namely by interfering with downstream or upstream actions of ras itself, are useful. Furthermore, the method of identification of said peptides utilizing calculational approaches is believed novel and has unexpectedly led us to these cyclic peptides and peptidomimetics disclosed herein.

SUMMARY OF THE INVENTION

The present invention provides peptidomimetics, peptides and cyclized peptides capable of inhibiting the oncogenic action of p21 ras.

This invention relates to peptidomimetics which model the critical semi-extended conformation of at least one peptide as set forth hereinbelow, exemplified by the compounds of Structure 1:

STRUCTURE 1

$$\text{OOC—(CH}_2)_m\text{—...}$$

wherein the sidechain R attached at the carbon atom numbered 6 on the sterol nucleus can be $NH—CH_2—CH_2NH_3^+$, alkyl amino, arylamino, or aralkylamino group, and wherein the sidechain attached at the carbon number 3 can be replaced with $—O—C(=O)—(CH_2)_m—COOH$, where m is an integer from 1 to 6, inclusive, preferably from 1 to 3, inclusive, and more preferably 2, and one of x and y at each position independently, can be one H, a small alkyl group of $C_1$ to $C_3$, preferably $C_1$; a halogen, preferably F, or an amino group where the other of one of x and y is H. Preferably, each of x and y is

STRUCTURE 2

$$\text{OOC—CH}_2\text{—...—NH—CH}_2\text{—CH}_2\text{—}^+NH_3$$

An exemplary compound falling within Structure 1 is 3 malonoxy-6-(2-aminoethyl) aminocyclopentanoperhydrophenanthrene (Structure 2).

The oncogenic ras-inhibiting cyclized peptides correspond to domains of the oncogenic ras protein which are most flexible and important in interacting with target proteins upstream and downstream from ras. The peptidomimetics are obtained by molecular modeling, including the structural minimization techniques of molecular dynamics. The peptides are designated by the formulas: Val-Val-Ile, Lys-Arg-Val, Ile-Lys-Arg-Val-Lys-Asp (SEQ ID NO:1), Lys-Cys-Asp-Leu-Ala (SEQ ID NO:2), Cys-Asp-Leu-Ala-Ala-Arg-Thr (SEQ ID NO:3), Asp-Leu-Ala-Ala (SEQ ID NO:4) or physiologically acceptable salts of the foregoing peptides.

Also provided in the present invention are cyclic analogues of the above peptides and certain others, namely:

cyclo[-R(1) R(2) Thr Ile Glu Asp Ser Tyr Arg Lys Gln Val Val Ile Asp R(3) R(4)-]  (I);

cyclo[-R(1) R(2) Val Val Ile R(3) R(4)-]  (II);

cyclo[-R(1) R(2) Tyr Arg Glu Gln Ile Lys Arg Val Lys Asp Ser Asp Asp Val Pro R(3) R(4)-]  (III);

cyclo[-R(1) R(2) Lys Arg Val R(3) R(4)-]  (IV);

cyclo[-R(1) R(2) Ile Lys Arg Val Lys Asp R(3) R(4)-]  (V);

cyclo[-R(1) R(2) Gly Asn Lys Cys Asp Leu Ala Ala Arg Thr Val Glu R(3) R(4)-]  (VI);

cyclo[-R(1) R(2) Lys Cys Asp Leu Ala R(3) R(4)-]  (VII);

cyclo[-R(1) R(2) Cys Asp Leu Ala Ala Arg Thr R(3) R(4)]  (VIII);

cyclo[-R(1) R(2) Asp Leu Ala Ala R(3) R(4)-]  (IX);

and

Furthermore, any amino acid in the sequences provided hereinabove may be replaced with its D-analogue, with the proviso that not more than 50% of the total amino acids are so replaced. Similarly, a homologous conservative substitution for any amino acid is within the bounds of the present invention provided that substitution does not eliminate the oncogenic ras p21-inhibiting activity. Thus, depending on the applications for which the peptides according to the invention are intended, it is also possible to envisage intercalating between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the isoleucine type, by leucine.

In addition, a subject polypeptide can differ, unless otherwise specified, from the natural sequences shown above by the sequence being modified by terminal —NH$_2$ acylation, e.g., acetylation, or by terminal-carboxylamidation, e.g., with ammonia, alkylamines, and the like.

DETAILED DESCRIPTION OF THE INVENTION

The natural sequence of the human oncogenic ras p21 is given in SEQ ID NO:5. The crystal X-ray structure has been determined at high resolution for that portion of the human ras protein corresponding to residues 1 to 166 of SEQ ID NO:5.

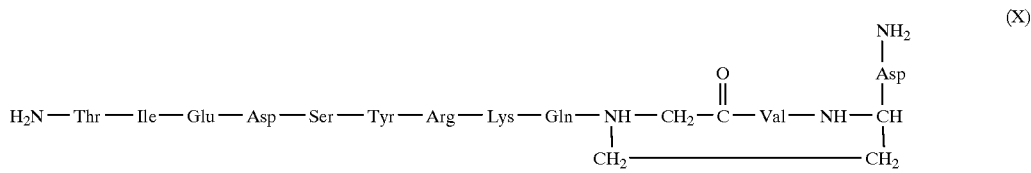

or physiologically acceptable salts thereof.

In cyclized peptide formulas (I)–(IX), R(1) R(2), R(3) and R(4) represent, in the most general case, any amino acid which can serve as an amino acid residue linker. Amino acid residue linkers are usually at least one residue and can be most often two to four residues, more often 1 to 10 residues, both ranges being inclusive. Typical amino acid residues useful for linking are tyrosine, cysteine, lysine, and glutamic and aspartic acid. Most preferably [R(1), R(2)] and [R(3), R(4)] are each independently selected from either the group consisting of Glu, Gln, Asp, Asn or from the group consisting of Lys, Arg, Orn.

The symbol - represents a bond between the carboxyl and amino termini by which R(1) and R(4) can be interconnected to each other via a lower alkenyl or lower alkynyl group, but most preferably by a branched or unbranched methylene bridge of type —(CH$_2$)$_m$— or —(CH$_2$)$_m$—M—(CH$_2$)$_{m'}$—. In such a moiety, m and m' are integers from 1 to 6, inclusive, and preferably from 1 to 3, inclusive; and M is NH, N[R(5)], O, S or CH—R(5), wherein R(5) is lower alkyl, cycloalkyl or aryl and is preferably methyl, ethyl, propyl, phenyl, X-phenyl, or heterocyclic, wherein X is Cl—, CF$_3$—, F—, substituted at the o-, m- , or p-positions on the phenyl group M can contain a part of another diamino acid within the same peptide, e.g., the omega amino group of the one residue can be so linked to such an unnatural amino acid residue in a terminal residue.

The regions of the p21 protein that are the most likely to change their conformations upon activation of the protein, e.g. by oncogenic amino acid substitutions have been computed using two different methods. Both methods are based on the principle that the linear sequence of amino acids in a protein determines its unique three-dimensional structure. Given an amino acid sequence of a polypeptide or protein, therefore, it should be possible to predict its three-dimensional structure. This task can be accomplished by using the principle that the observed three-dimensional structure of a protein is the one of lowest free energy. There are a vast number of possible structures a given polypeptide chain can adopt, but essentially only one of these is observed. To allow folding to occur, therefore, the interatomic interactions in the protein chain must greatly stabilize its final folded form, i.e., lower its conformational energy substantially with respect to that of any other competing structure. Thus, to compute the lowest energy form of a protein, it is necessary to be able first to compute the conformational energy of a given conformation of the protein and then, second, to generate its low energy conformations, or a representative sampling of them. The structure of lowest conformational energy so computed is then predicted to be the observed structure of the protein. This structure may be the one determined by x-ray crystallography or by 2- or 3-dimensional nuclear magnetic resonance (NMR) techniques.

A set of potential energy functions, in the computer program ECEPP (Empirical Conformational Energies of Peptides Program), have been developed that accurately compute the conformational energies of given conformations of proteins. The conformational energy of a peptide can be expressed in Equation 1.

$$E_{tot} = \sum_{i \neq j} \frac{Q_i Q_j}{D R_{ij}} + \sum_{i \neq j} \epsilon_{ij} \left( \left[ \frac{\rho_{ij}}{R_{ij}} \right]^{12} - 2 \left[ \frac{\rho_{ij}}{R_{ij}} \right]^6 \right) + \sum_k \left( \frac{A_k}{2} \right) (1 \pm \cos(n\Theta_k))$$

where $E_{tot}$ is the total conformational energy of the protein, the Q's are the charges on the $i^{th}$ and $j^{th}$ atoms; $R_{ij}$ is the distance between the $i^{th}$ and $j^{th}$ atoms, D is the dielectric constant, $\epsilon_{ij}$ and $\sigma_{ij}$ are the lowest non-bonded (Lennard-Jones) energy and the distance at this lowest energy between atoms i and j in the protein; $A_k$ is the torsional barrier to rotation around specific bonds; $\Theta_k$ is the $k^{th}$ dihedral angle in the protein; n is a degeneracy factor, i.e., 3 for single bonds and 2 for double bonds; and the sign in the last summation term is positive for single bonds and negative for double bonds such as occur in the peptide bond units.

This equation shows the total conformational energy as the sum of three terms: the pairwise electrostatic interactions between the individual atoms of a protein, each of which has a partial charge, (first sum); a non-bonded energy term (second term) that consists of an attractive term that varies as the inverse sixth power (tenth power for hydrogen-bonding atoms) of the distance between the atoms (from an induced dipole-induced dipole interaction term) and a repulsive term, from the overlap of electron shells, that varies as the inverse twelfth power of the interatomic distance; and finally a torsional term (third sum) that depends upon the bonds about which rotation takes place. All of the constants in these terms have been determined from experimental crystal packing data and reproduce the lattice constants of all of the crystal structures of small molecules to which they have been applied and, where measured, the sublimation energies of these crystals. These potential functions have been used to compute the low energy minima for single terminally blocked amino acid residues, simple peptides, oligopeptides, polypeptides, and proteins with excellent agreement between the lowest energy predicted structures and the structures determined experimentally. These potentials have therefore been well-tested, are based on experimental data, and have proved to be reliable in prediction of structure from sequence.

These potential functions have been used to compute the average structure for the ras-p-21 protein in its normal and in its oncogenic form using the perturbation method called the electrostatically-driven Monte Carlo method (EDMC). Specific regions of the oncogenic p21 protein undergo large conformational changes compared with the structure of the normal, inactive protein. One of these regions has been found to be residues 35–47. All of the segments that change conformation in the oncogenic protein were found to be the most flexible in the normal, inactive protein.

Of considerable significance has been the finding that a completely different method, viz. molecular dynamics, based upon a completely different set of potential functions, i.e. the program DISCOVER, yields identical results for the p21 protein.

Molecular dynamics is based on the principle that the positions of the atoms of a molecule can be predicted as a function of time by solving Newton's equations of motion for the molecule. The force on the molecule is the negative of the first derivative of the potential function with respect to the coordinates of each of the atoms. Newton's equations of motion are then integrated, using the Verlet algorithm, over a trajectory such that the low energy regions around the starting structure are computed. The trajectories are computed over time intervals such that the total energy converges to a low, constant value. The structures whose energies have converged are then used to compute an average structure. Comparison of the coordinates of the atoms of this average structure with those of the starting structure reveals regions of the protein whose conformations may change significantly. Furthermore, if the variance of the coordinates of regions of the low energy structures from the corresponding coordinates of the average structure are high, these regions can be identified as being flexible, i.e., are the ones most likely to be parts of effector domains. Within this algorithm, for the p21 protein, up to 2000 water molecules have been generated around the protein in the molecular dynamics simulations performed thus far.

Using these novel calculational approaches, the present inventors have identified important peptide regions of the protein that are involved in the signal transduction process, and these peptides can be used to design anti-cancer agents, as taught herein. We have found that most particularly the 35–47, 96–110 and 115–126 peptides have strong and specific anti-oncogenic p21 activity. Even more particularly, we found that these domains contain unique extended structures and/or short beta-bend structures which are hypothesized to account in large part for their biological uniqueness. This suggested that cyclization of the peptide structures to force the beta-bend conformation in place would serve to enhance therapeutic activity.

The results of these studies indicate that a domain of particular interest is the domain from residues 35 through 47 of SEQ ID NO:5, i.e., Thr-Ile-Glu-Asp-Ser-Tyr-Arg-Lys-Gln-Val-Val-Ile-Asp (SEQ ID NO:6), of even more particular interest the peptide corresponding to residues 44 to 46 in SEQ ID NO:5, i.e., Val-Val-Ile, of still more interest is the sequence from residues 96 to 110 of SEQ ID NO:5, i.e., Tyr-Arg-Glu-Gln-Ile-Lys-Arg-Val-Lys-Asp-Ser-Asp-Asp-Val-Pro (SEQ ID NO:7), of even more particular interest is the sequence from residues 101–103 in SEQ ID NO:5, i.e., Lys-Arg-Val; and the sequence corresponding to residues 100 to 105 in SEQ ID NO:5, i.e., Ile-Lys-Arg-Val-Lys-Asp (SEQ ID NO:1); the sequence corresponding to residues 115 to 126 of SEQ ID NO:5, i.e., Gly-Asn-Lys-Cys-Asp-Leu-Ala-Ala-Arg-Thr-Val-Glu (SEQ ID NO:8); and most particularly the sequence corresponding to residues 117 to 121 of SEQ ID NO:5, i.e, Lys-Cys-Asp-Leu-Ala (SEQ ID NO:2) and the sequence corresponding to residues 118 to 124 of SEQ ID NO:5, i.e., Cys-Asp-Leu-Ala-Ala-Arg-Thr (SEQ ID NO:9); and the sequence corresponding to residues 119 to 122 of SEQ ID NO:5, i.e., Asp-Leu-Ala-Ala (SEQ ID NO:4).

Additional sequences homologous to the various preferred sequences recited hereinabove can be derived by one skilled in the art from the sequences of closely related ras proteins. Such sequences may possess enhanced therapeutic activity. Nonlimiting examples of such proteins closely related to the ras gene product which represent the parent sequences having identical or nearly identical three dimensional structures and from which homologs of the sequences given in the preceding paragraph can be derived by one normally skilled in the art are:

ras-related protein Ara-3 [*Arabidopsis thaliana* (mouse ear cress)] (SEQ ID NO:10);
ras-related protein Ara-2 [*A. thaliana*] SEQ ID NO:11;
ras-related protein Ara-1 [*A. thaliana*] SEQ ID NO:12;

ras-related protein OraB-1 [*Discopyge ommata* (electric ray)] SEQ ID NO:13;
ras-related protein Rab-1A [*Lymnea stagnalis* (great pond snail)] SEQ ID NO:14;
ras-related protein Rab-2 [*Homo sapiens* (human)] SEQ ID NO:15;
ras-related protein Rab-2 [*L. stagnalis*] SEQ ID NO:16;
ras-related protein Rab-2 [*Oryctolagus cuniculus* (rabbit)] SEQ ID NO:17;
ras-related protein Rab-2 [*Rattus norvegicus* (rat)] SEQ ID NO:18;
ras-related protein Rab-3 [*Drosophila melanogaster* (fruitfly)] SEQ ID NO:19;
ras-related protein Rab-4 [*R. norvegicus*] SEQ ID NO:20;
ras-related protein Rab-6 [*Caenorhabditis elegans*] SEQ ID NO:21;
ras-related protein Rab-6 [*H. sapiens*] SEQ ID NO:22;
ras-related protein Rab-7 [*Canis familiaris* (dog)] SEQ ID NO:23;
ras-related protein Rab-7 [*Dictyostelium discoideum* (slime mold)] SEQ ID NO:24;
ras-related protein Rab-8 [*C. familiaris*] SEQ ID NO:25;
ras-related protein RabC [*D. discoideum*] SEQ ID NO:26;
ras-related protein Rac-1 [*C. elegans*] SEQ ID NO:27;
ras-related protein Rac-1A [*D. discoideum*] SEQ ID NO:28;
ras-related protein RacB [*D. discoideum*] SEQ ID NO:29;
ras-related protein RacC [*D. discoideum*] SEQ ID NO:30;
ras-related protein Ral-A [*H. sapiens*] SEQ ID NO:31;
ras-related protein Ral-B [*H. sapiens*] SEQ ID NO:32;
ras-related protein O-Ral [*D. ommata*] SEQ ID NO:33;
ras-related protein Ora-1 [*D. ommata*] SEQ ID NO:34;
ras-related protein Ora-2 [*D. ommata*] SEQ ID NO:35;
ras-related protein Ora-3 [*D. ommata*] SEQ ID NO:36;
ras-related protein Rap-1 [*D. discoideum*] SEQ ID NO:37;
ras-related protein Rap-2A [*H. sapiens*] SEQ ID NO:38;
ras-related protein Rap-2B [*H. sapiens*] SEQ ID NO:39;
ras-related protein O-KREV [*D. ommata*] SEQ ID NO:40;
ras-related protein Rap-1A [*H. sapiens*] SEQ ID NO:41;
ras-related protein Rap-1B [*H. sapiens*] SEQ ID NO:42;
ras-like protein GNROR3 [*D. melanogaster*] SEQ ID NO:43;
ras-like protein rasA [*D. discoideum*] SEQ ID NO:44;
ras-like protein rasB [*D. discoideum*] SEQ ID NO:45;
ras-like protein racC [*D. discoideum*] SEQ ID NO:46;
ras-like protein rasG [*D. discoideum*] SEQ ID NO:47;
ras-like protein F54C8.5 [*C. elegans*] SEQ ID NO:48;
ras-like protein CC-ras [*Coprinus cinereus* (inky cap fungus)] SEQ ID NO:49;
ras-like protein [*Geodia cydonium* (sponge)] SEQ ID NO:50;
ras-related protein Rab-10 [*C. familiaris*] SEQ ID NO:51;
ras-related protein Rab-11 [*H. sapiens*] SEQ ID NO:52.

In addition, as described hereinabove, the therapeutic activity of these sequences is enhanced by cyclization. Cyclization forces and maintains the conformations of these peptides in unique structures like beta-bends. The following are representative, nonlimiting examples of cyclized peptides useful for inhibiting the oncogenic activity of the ras protein, said peptides having formulas as given below:

cyclo[-R(1) R(2) THR ILE GLU ASP SER TYR ARG LYS GLN VAL VAL ILE ASP R(3) R(4)-]  (I)

cyclo[-R(1) R(2) VAL VAL ILE R(3) R(4)-]  (II)

cyclo[-R(1) R(2) TYR ARG GLU GLN ILE LYS ARG VAL LYS ASP SER ASP ASP VAL PRO R(3) R(4)-]  (III)

cyclo[-R(1) R(2) LYS ARG VAL R(3) R(4)-]  (IV)

cyclo[-R(1) R(2) ILE LYS ARG VAL LYS ASP R(3) R(4)-]  (V)

cyclo[-R(1) R(2) GLY ASN LYS CYS ASP LEU ALA ALA ARG THR VAL GLU R(3) R(4)-]  (VI)

cyclo[-R(1) R(2) LYS CYS ASP LEU ALA R(3) R(4)-]  (VII)

cyclo[-R(1) R(2) CYS ASP LEU ALA ALA ARG THR R(3) R(4)-]  (VIII)

cyclo[-R(1) R(2) ASP LEU ALA ALA R(3) R(4)-]  (IX);

and

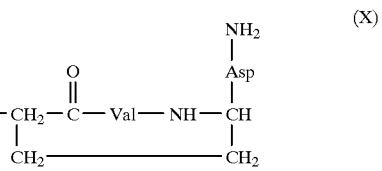

or a physiologically acceptable salt thereof.

In the aforementioned cyclized peptide formulas R–IX, R(1) R(2), R(3) and R(4) represent, in the most general case, any amino acid, such that they serve as amino acid residue linkers. Amino acid residue linkers are usually at least one residue and can be most often two to four residues, more often 1 to 10 residues. Typical amino acid residues used for linking are tyrosine, cysteine, lysine, glutamic and aspartic acid. Most preferably [R(1), R(2)] and [R(3), R(4)] independently are selected from either the groups [Glu, Gln, Asp, Asn] or [Lys, Arg, Orn].

The term - represents a bond between the carboxyl and amino termini by which R(1) and R(4) can be interconnected to each other via a lower alkyl, alkenyl or lower alkynyl group, but most preferably by a branched or unbranched methylene bridge of type —(CH$_2$)$_m$— or —(CH$_2$)$_m$—M—(CH$_2$)$_{m'}$. In such a moiety, m and m' are integers from 1 to 6, inclusive, and preferably from 1 to 3, inclusive; and M is NH, N[R(5)], O, S or CH-R(5), wherein R(5) is lower alkyl, cycloalkyl or aryl and is preferably methyl, ethyl, propyl, phenyl, X-phenyl, or heterocyclic, wherein X is Cl—, CF$_3$, F—, substituted at the o-, m- , or p-positions on the phenyl group. M can contain a part of another diamino acid within the same peptide, e.g., the omega amino group of the one residue can be so linked to such an unnatural amino acid residue in a terminal residue.

Furthermore, any amino acid in the cyclized peptide sequences (I)–(X) recited herein may be replaced with its D-analogue, insofar as not more than 50% of the total amino acids are so replaced. Similarly, a homologous conservative substitution for any amino acid is within the bounds of the present invention. Conservative substitutions include Glu for Asp, Gln for Asn and Val for Ile, among others, as well-known to the art. Depending on the applications for which the peptides according to the invention are intended, it is also possible to intercalate between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the proline type, by D-tryptophan.

In addition, a subject polypeptide can differ, unless otherwise specified, from any of the natural sequences shown herein above by the sequence being modified by terminal —NH₂ acylation, e.g., acetylation, or by terminal-carboxylamidation, e.g., with ammonia, alkylamines, and the like.

The placement of hydrophobic amino acid residues is highly dependent on the peptide sequence. For example, for the 35–47 peptide sequence, corresponding to amino acids 35–47 of SEQ ID NO:5, there is a distinct hydrophobic region for the amino acid residues corresponding to amino acids 44–46 of SEQ ID NO:5. The bridge in Compound (X) occurs at what corresponds in structure to amino acids 44–46 in SEQ ID NO:5. It is possible to extend this hydrophobic segment without sacrificing activity. For example, the carboxyl terminal Asp residue can be replaced with one or more hydrophobic residues such as Val or Ile, and the result is greater efficiency in crossing cell membranes.

Short half-lives of peptides, a major problem, can be at least partially extended by the addition of D-amino acids to either or both of the amino and carboxyl terminal ends of the peptide. These D-amino acid residues block the action of exo-proteases that degrade peptides from their amino or carboxyl ends. In addition, the cyclization of the peptide further renders the peptide less susceptible to proteolysis.

Recent advances in the field of peptides have been directed towards the stabilization of these peptides against enzymatic or hydrolytic degradation. It would be extremely valuable to stabilize these peptides from degradation by proteolytic enzymes in order to improve their pharmacokinetic properties. Enhanced resistance to enzymatic degradation would increase the usefulness of these peptides as therapeutic agents. However, since they only exhibit short half lives in vivo, large amounts of such peptides must typically be administered to a subject in order to achieve the desired effect. Alternatively, smaller quantities may be prescribed to an individual, but more frequent dosages would be required to achieve the same level of potency.

It is further well-known to those normally skilled in the art that it is possible to replace peptides with peptidomimetics. Peptidomimetics are generally preferable as therapeutic agents to peptides owing to their enhanced bioavailability and relative lack of attack from proteolytic enzymes. The present inventors have used the techniques of molecular modeling supra to design a peptidomimetic which mimics the critical beta-bend aspects of the peptide corresponding in sequence to amino acids 96–110 of SEQ ID NO:5 (p21 ras). The bend structure occurs at amino acids 102–103 in the p21 ras protein. These residues have been implicated in the binding of ras p21 to SOS.

Peptidomimetic compounds which inhibit the oncogenic or transforming activity of the p21 ras protein are provided by the compounds of Structure I:

STRUCTURE I

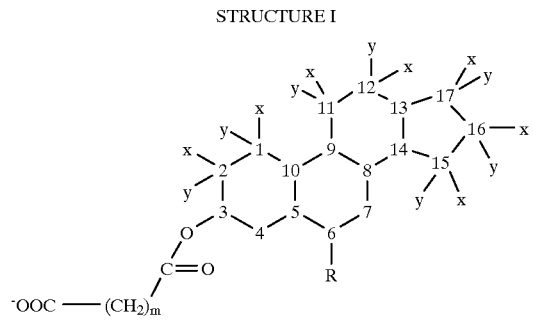

wherein the sidechain R attached at the carbon atom numbered 6 on the sterol nucleus can be NH—CH₂—CH₂NH₃⁺, alkyl amino, arylamino, or aralkylamino group, and wherein the sidechain attached at the carbon number 3 can be replaced with —O—C(=O)—CH₂)ₘ—COOH, where m is an integer from 1 to 6, inclusive, preferably from 1 to 3, inclusive, and more preferably 2, and one of x and y at each position independently, can be one H, a small alkyl group of C₁ to C₃, preferably C₁; a halogen, preferably F, or an amino group where the other of one of x and y is H. Preferably, each of x and y is H.

Without wishing to be bound by any particular theory, the structure believed to be the optimally designed ras-inhibiting peptidomimetic is illustrated below in Structure II:

STRUCTURE 2

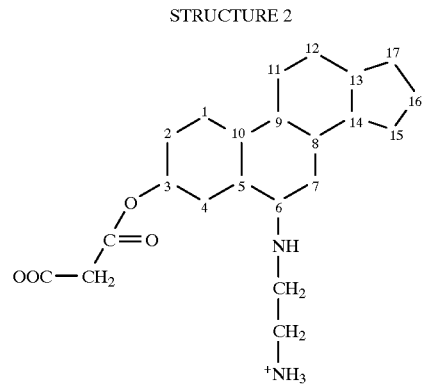

The instant invention comprises novel peptides of medicinal importance most particularly for the treatment of adenocarcinomas of the colon, pancreatic carcinomas, neuroblastomas, and other cancers of undefined germ cell origin which express the transformed sequence of the ras protein. These peptide sequences were unexpectedly obtained by the use of molecular dynamic simulations on ras p21 to define which domains of the protein were most flexible and were thus most important in interacting with target proteins upstream and downstream from ras. These peptides are identified by the following amino acid sequences: Thr-Ile-Glu-Asp-Ser-Tyr-Arg-Lys-Gln-Val-Val-Ile-Asp (SEQ ID NO:6), Val-Val-Ile, Tyr-Arg-Glu-Gln-Ile-Lys-Arg-Val-Lys-Asp-Ser-Asp-Asp-Val-Pro (SEQ ID NO:7), Lys-Arg-Val, Ile-Lys-Arg-Val-Lys-Asp (SEQ ID NO:1), Gly-Asn-Lys-Cys-Asp-Leu-Ala-Ala-Arg-Thr-Val-Glu (SEQ ID NO:8), Lys-Cys-Asp-Leu-Ala (SEQ ID NO:2), Cys-Asp-Leu-Ala-Ala-Arg-Thr (SEQ ID NO:9), and Asp-Leu-Ala-Ala (SEQ ID NO:4).

Including the cyclic analogues of the above peptides, namely:

cyclo[-R(1) R(2) Thr-Ile-Glu-Asp-Ser-Tyr-Arg-Lys-Gln-Val-Val-Ile-Asp-R(3) R(4)-] (I);

cyclo[-R(1) R(2) Val-Val-Ile-R(3) R(4)-] (II);

cyclo[-R(1) R(2) Tyr-Arg-Glu-Gln-Ile-Lys-Arg-Val-Lys-Asp-Ser-Asp-Asp-Val-Pro-R(3) R(4)-] (III);

cyclo[-R(1) R(2) Lys-Arg-Val R(3) R(4)-] (IV);

cyclo[-R(1) R(2) Ile-Lys-Arg-Val-Lys-Asp R(3) R(4)-] (V);

cyclo[-R(1) R(2) Gly-Asn-Lys-Cys-Asp-Leu-Ala-Ala-Arg-Thr-Val-Glu R(3) R(4)-] (VI);

cyclo[-R(1) R(2) Lys-Cys-Asp-Leu-Ala R(3) R(4)-] (VII);

cyclo[-R(1) R(2) Cys-Asp-Leu-Ala-Ala-Arg-Thr R(3) R(4)-] (VIII);

cyclo[-R(1) R(2) Asp-Leu-Ala-Ala R(3) R(4)-]Z (IX);

and vative substitutions include Glu for Asp, Gln for Asn and Val for Ile, among others, as is well known to those of ordinary skill in the art. Similarly, a homologous conservative substitution for any amino acid is within the bounds of the present invention. Depending on the applications for which the peptides according to the invention are intended, it is also possible to envisage intercalating between several amino acids, or even between all the amino acids, of the peptides defined above, dextrorotatory amino acids, and in particular dextrorotatory phenylalanine or dextrorotatory tryptophan, capable of preventing the action of the degradative enzymes in the cell environment and thus of increasing their activity. Another modification in this sense consists in replacing certain amino acids, for example of the proline type, by D-tryptophan.

In addition, a subject polypeptide can differ, unless otherwise specified, from the natural sequences shown above by the sequence being modified by terminal —NH$_2$ acylation, e.g., acetylation, or by terminal-carboxylamidation, e.g., with ammonia, alkylamines, and the like.

The instant invention also comprises a method of use of the peptides supra for the treatment of adenocarcinomas of the colon, pancreatic carcinomas, neuroblastomas, and other cancers of undefined germ cell origin which express the transformed sequence of the ras protein.

It is also an object of the present invention to provide peptides and cyclized peptide homologs from the sequences listed in SEQ ID NOs:10–52.

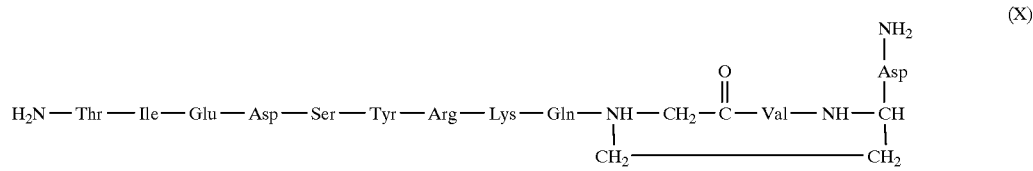

or a physiologically acceptable salt thereof.

Wherein for cyclized peptide formulas designated by (I)–(IX) hereinabove, R(1) R(2), R(3) and R(4) represent, in the most general case, any amino acid, such that they serve as amino acid residue linkers. Amino acid residue linkers are usually at least one residue and can be most often two to four residues, more often 1 to 10 residues. Typical amino acid residues used for linking are tyrosine, cysteine, lysine, glutamic and aspartic acid, or the like. Most preferably [R(1), R(2)] and [R(3), R(4)] independently are selected from either the groups [Glu, Gln, Asp, Asn] or [Lys, Arg, Orn].

The symbol - represents a bond between the carboxyl and amino termini by which R(1) and R(4) can be interconnected to each other via a lower alkenyl or lower alkynyl group, but most preferably by a branched or unbranched methylene bridge of type —(CH$_2$)$_m$— or —(CH$_2$)$_m$—M—(CH$_2$)$_{m'}$—. In such a moiety, m and m' are integers from 1 to 6 and preferably from 1 to 3; and M is NH, N[R(5)], O, S CH-R(5) or does not exist, wherein R(5) is lower alkyl, cycloalkyl or aryl and is preferably methyl, ethyl, propyl, phenyl, X-phenyl, or heterocyclic, wherein X is Cl—, CF$_3$—, F—, substituted at the o-, m- , or p-positions on the phenyl. M can contain a part of another diamino acid within the same peptide, e.g., the omega amino group of the one residue can be so linked to such an unnatural amino acid residue in a terminal residue.

Furthermore, any amino acid in the sequences provided may be replaced with its D-analogue, insofar as not more than 50% of the total amino acids are so replaced. Conser- The amino acid residues described herein are preferred to be in the "L" isomeric form. However, residues in the "D" isomeric form can be substituted for any L-amino acid residue, as long as the desired functional property is retained by the polypeptide. NH$_2$ refers to the free amino group present at the amino terminus of a polypeptide. COOH refers to the free carboxyl group present at the carboxy terminus of a polypeptide. In keeping with standard polypeptide nomenclature described in J. Biol. Chem. 243:3552–3559 (1969) and adopted at 37 C.F.R. 1.822(b) (2). The list of variable amino acids capable of participating in the composition of this peptide is as follows: Y, Tyr, tyrosine; G, Gly, glycine; F, Phe, phenylalanine; M, Met, methionine; A, Ala, alanine; S, Ser, serine; I, Ile, isoleucine; L, Leu, leucine; T, Thr, threonine; V, Val, valine; P, Pro, proline; K, Lys, lysine; H, His, histidine; Q, Gln, glutamine; E, Glu, glutamic acid; W, Trp, tryptophan; R, Arg, arginine; D, Asp, aspartic acid; N, Asn, asparagine; C, Cys, cysteine.

Amino acid residue sequences are presented herein in the conventional left-to-right direction of amino-terminus to carboxy-terminus. In addition, the phrase "amino acid residue" is broadly defined to include the amino acids listed hereinabove, and modified and unusual amino acids, such as those listed in 37 C.F.R. 1.822(b) (4), incorporated herein by reference. Furthermore, it should be noted that a dash at the beginning or end of an amino acid residue sequence indicates either a peptide bond to a further sequence of one or more amino acid residues or a covalent bond to an amino or hydroxyl end group.

Polypeptide and peptide are terms used interchangeably herein to designate a linear series of amino acid residues connected one to the other by peptide bonds between the alpha-amino and carboxy groups of adjacent residues.

Protein is a term used herein to designate a linear series of greater than about 20 amino acid residues connected one to the other as in a polypeptide.

The term synthetic peptide refers to a chemically produced chain of amino acid residues linked together by peptide bonds that is free of naturally occurring proteins and fragments thereof. The term peptide encompasses linear and cyclic peptides.

(D,L), (D), or (L) preceding the amino acid designation means that this amino acids exists in that specific isomeric form, i.e. (D,L) Phe means that the amino acid phenylalanine exists as a racemic mixture; (D) Phe or D-Phe means that the amino acid phenylalanine exists as the D-stereoisomer or implied R configuration; (L) Phe means that the amino acid phenylalanine exists as the L stereoisomer or implied S configuration.

Alkyl as used herein means methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, 1-methyl-1-propylbutyl.

Cycloalkyl refers to a hydrocarbon ring having from 3 to 7 carbon atoms, inclusive. Examples of cycloalkyl groups are cyclopropyl, cyclopentyl, cycloheptyl, cyclooctyl, cyclononyl, and the like.

The term aryl refers to aromatic groups which have at least one ring having a conjugated pi electron system and includes carbocyclic aryl, heterocyclic aryl aralkyl, and biaryl groups, all of which may be optionally substituted.

Heterocyclic groups means groups having from 1 to 3 heteroatoms as ring atoms in the aromatic ring and the remainder of the ring atoms carbon atoms. Suitable heteroatoms include oxygen, sulfur, and nitrogen, and their heterocyclic compands can include furanyl, thienyl, pyridyl, pyrrolyl, N-lower alkyl pyrrolo, pyrimidyl, pyrazinyl, imidazolyl, and the like, all optionally substituted.

Substituted heterocyclic refers to any heterocyclic aryl group substituted by a alkyl, aryl, cycloalkyl, halo, sulfonate, or trifluoromethyl group.

The term alkyl amino refers to the groups —NRR' wherein respectively, (a) R is alkyl and R' is hydrogen or alkyl; (b) R is aryl and R' is hydrogen or aryl, (c) R is cycloalkyl and R' is hydrogen or alkyl, (d) R is hydrogen and R' is itself linear aminoalkyl, (e) R is alkyl and R' is itself linear aminoalkyl.

The term aminoalkyl refers to the groups —$(CH_2)_m$—NRR', wherein m is an integer from 1 to 6, inclusive and —NRR' is alkyl amino, as defined supra.

Halo encompasses fluoro, chloro, bromo and iodo.

The phrase protecting group, as used herein, means substituents which protect the reactive functional group from undesirable chemical reactions. Examples of such protecting groups include esters of carboxylic acids, ethers of alcohols and acetals and ketals of aldehydes and ketones.

The phrase N-protecting group or N-protected as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly. The deprotection conditions for the above protecting groups necessarily vary with the choice of protecting group. Thus, for example, an acyl group such as an alkanoyl, alkoxycarbonyl or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid such as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-charcoal.

The phrase COOH-protecting group or carboxyl-protecting group is, an esterifying group, for example an alkyl group (especially methyl or ethyl) or an arylmethyl group (especially benzyl). The deprotection conditions for the above protecting groups necessarily vary with the choice of protecting group. Thus, for example, an esterifying group such as an alkyl or arylmethyl group may be removed, for example, by hydrolysis with a suitable base such as an alkali metal hydroxide, for example lithium or sodium hydroxide. Alternatively an esterifying group such as an arylmethyl group may be removed, for example, by hydrogenation over a catalyst such as palladium-on-charcoal using either hydrogen or ammonium formate as a hydrogen source by methods well-known to those skilled in the art.

Electrolyte means a solution that has sufficient acid strength to render a basic starting material essentially protonated.

Chemical derivative refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imidazolyl-benzylhistidine. Also included as chemical derivatives are those peptides which contain one or more naturally occurring amino acid derivatives of the twenty standard amino acids. For examples, 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

As used herein, fragment means any subject peptide or polypeptide having an amino acid residue sequence shorter than that of a peptide or polypeptide whose full length amino acid residue sequence is shown herein.

A pharmaceutically acceptable salt is one which is prepared by contacting a compound of formulas (I)–(X) according to the specifications therein with an acid whose anion is generally considered suitable for human consumption. Examples of pharmacologically acceptable acid addition salts include the hydrochloride, hydrobromide, hydroiodide, sulfate, phosphate, acetate, propionate, lactate, maleate, malate, succinate, and tartrate salts. All of these salts may be prepared by conventional means by reacting, for example, the appropriate acid with the corresponding compound of structure of Formulas (I)–(X).

Unless otherwise indicated, the preparation methods disclosed herein result in product distributions which include all possible structural isomers. It is understood that physiological response may vary according to stereochemical structure. The isomers may be separated by conventional means such as fractional crystallization or High Pressure Liquid Chromatography (HPLC). Briefly, the absolute configuration of a compound relates to how its substituents are oriented in space about a central atom. This notion becomes significant when coupled with the rigors of chirality. Chirality involves the identity of the substituents about that central atom. Thus, in general, a compound is said to be chiral when four distinctly different groups are bound to a central carbon atom. These groups may be spatially aligned in more than one manner without repeating their individual orientations. That is, a chiral compound may exhibit a mirror image which is also chiral. These mirror images are termed meso configurations, and are each absolute configurations of a chiral compound.

Pharmaceutical compositions according to the present invention comprise peptidomimetics of the present invention in association with a pharmaceutically acceptable carrier or excipient, adapted for use in human or veterinary medicine. Optionally, the pharmaceutical composition can further include at least one peptide or cyclic peptide of the present invention. The compositions may contain from 0.001–99% of the active material. Such compositions may be presented for use in conventional manner in admixture with one or more physiologically acceptable carriers of excipients. The pharmaceutical compositions according to the invention may also contain other active ingredients such as antimicrobial agents, or preservatives. The compositions may optionally further contain one or more other therapeutic agents which may, if desired, be a chemotherapeutic antiviral agent. It is understood that these compositions must include the active ingredients (peptidomimetic, peptide, cyclic peptide) in an amount effective for the inhibition of the oncogenic and/or transforming activity of the p21 ras oncogenic protein.

Pharmaceutically acceptable salts of the peptides of this invention may be formed conventionally by reaction with an appropriate acid. The addition salts so formed from addition by acid may be identified by hydrochloric, hydrobromic, phosphoric, acetic, fumaric, salicylic, citric, lactic, mandelic, tartaric, oxalic, methanesulfonic, and the like.

Thus, the peptides and peptidomimetics according to the present invention may be formulated for oral, buccal, parenteral, topical or rectal administration. In particular, these peptides and peptidomimetics may be formulated for injection or for infusion and may be presented in unit dose form in ampoules or in multidose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, e.g. sterile, pyrogen-free water, before use.

The present invention further provides a process for preparing a pharmaceutical composition which comprises bringing a peptide and/or peptidomimetic of the invention into association with a pharmaceutically acceptable excipient or carrier.

For administration by injection or infusion, the daily dosage as employed for treatment of an adult human of approximately 70 kg body weight will range from 0.01 mg to 10 mg of each active ingredient, preferably 0.1 to 5 mg, which may be administered in 1 to 4 doses, for example, depending on the route of administration and the condition of the patient. The dosage of the peptide used in the treatment will vary depending on the seriousness of the disorder, the weight of the patient, the relative efficacy of the peptide and the judgment of the treating physician. However, suitable unit dosages in humans may be between about 0.05 mg to about 100 mg. For example, a unit dosage may be from between about 0.2 mg to about 50 mg. Such a unit dosage, described hereinabove, may be administered more than once a day, e g., two or three times a day. Thus, the total daily dosage is in the range of about 0.01 mg to 10 mg/kg. Such therapy may extend for several weeks, in an intermittent or uninterrupted manner, until the patient's symptoms are eliminated.

The present invention also provides pharmaceutical compositions which comprise a pharmaceutically effective amount of one or more peptidomimetics and/or peptides of this invention, or pharmaceutically acceptable salts thereof, and, preferably, a pharmaceutically acceptable carrier or adjuvant. Therapeutic methods of this invention comprise the step of treating patients in a pharmaceutically acceptable manner with those peptides or compositions. Such compositions may be in the form of tablets, capsules, caplets, powders, granules, lozenges, suppositories, reconstitutable powders, or liquid preparations, such as oral or sterile parenteral solutions or suspensions.

In order to obtain consistency of administration, it is preferred that a composition of the invention is in the form of a unit dose. The unit dose presentation forms for oral administration may be tablets and capsules and may contain conventional expedients. For example binding agents, such as acacia, gelatin, sorbitol, or polyvinylpyrrolidone; fillers, such as lactose, sugar, maize-starch, calcium phosphate, sorbitol or glycine; tabletting lubricants, such as magnesium stearate; disintegrants, such as starch, polyvinylpyrrolidone, sodium starch glycolate or microcrystalline cellulose; or pharmaceutically acceptable wetting agents, such as sodium lauryl sulfate.

The solid oral compositions may be prepared by conventional methods of blending, filling, tabletting, or the like. Repeated blending operations may be used to distribute the active agent throughout those compositions employing large quantities of fillers. Such operations are, of course, conventional in the art. The tablets may be coated according to methods well-known in normal pharmaceutical practice, in particular with an enteric coating.

Oral liquid preparations may be in the form of emulsions, syrups, or elixirs, or may be presented as a dry product for reconstitution with water or other suitable vehicle before use. Such liquid preparations may or may not contain conventional additives. For example, suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl parahydroxybenzoate, ethyl para-hydroxybenzoate, n-propyl parahydroxybenzoate, or n-butyl parahydroxybenzoate or sorbic acid; and, if desired, conventional flavoring or coloring agents.

For parenteral administration, fluid unit dosage forms may be prepared by utilizing the peptide and a sterile vehicle, and, depending on the concentration employed, may be either suspended or dissolved in the vehicle. In preparing solutions, the peptides of this invention may be dissolved in water, whereas opiates used heretofore showed only marginal solubility in aqueous media or physiological fluids. Once in solution, the peptide may be injected and filter sterilized before filling a suitable vial or ampoule and subsequently sealing the carrier or storage package. Adjuvants, such as a local anaesthetic, a preservative or a buffering agent, may be dissolved in the vehicle prior to use. Stability of the pharmaceutical composition may be enhanced by freezing the composition after filling the vial and removing the water under vacuum, e.g., freeze drying the composition. Parenteral suspensions may be prepared in substantially the same manner, except that the peptide should be suspended in the vehicle rather than being dissolved. A surfactant or wetting solution may be advantageously included in the composition to facilitate uniform distribution of the peptide.

The stability of the peptides and cyclic peptides of the present invention exceeds that of naturally occurring peptides if substitution is made with D-amino acids in at least 20%, but not more than 50%, of those residues which are naturally present in the (L) configuration. Without being bound by theory, we believe that the increased resistance to enzymatic degradation of the peptides of the present invention as compared to natural peptides is due to the presence of D-amino acids in the peptides. This switch from L to D amino acids neutralizes the digestion capabilities of many of the ubiquitous peptidases found in the digestive tract. Alternatively, the enhanced stability of the peptides of this invention may also be the result of the introduction of modifications of traditional peptide linkages. For example, the introduction of a cyclic ring within the peptide backbone may confer enhanced stability in order to circumvent the effect of many proteolytic enzymes known to digest small peptides in the stomach or other digestive organs and in serum.

The compounds of the present invention are initially synthesized by either solution or by solid phase techniques. Specific exemplary syntheses are described in the examples hereinbelow. The peptides of this invention may be prepared by initially reacting a first appropriately protected amino acid with a second appropriately protected amino acid in an organic solvent inert to the reactants, in the presence of a suitable peptide coupling agent according to the following scheme:

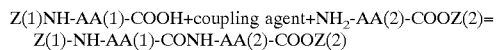
Z(1)NH-AA(1)-COOH+coupling agent+NH$_2$-AA(2)-COOZ(2)=
Z(1)-NH-AA(1)-CONH-AA(2)-COOZ(2)

wherein Z(1) is a suitable nitrogen protecting group and Z(2) is a suitable carboxyl protecting group and AA represents any natural or unnatural amino acid residue. The desired peptides may be prepared by utilizing the appropriate amino acids and repeating this reaction sequence as required until a peptide with three to ten amino acid residues has been prepared. A suitable deprotection method is then employed to remove specified or all of the remaining protecting groups or the peptide from the resin.

The first appropriately protected amino acid and, for instance, an appropriately protected tyrosine may be reacted together in the presence of a suitable peptide coupling agent in a suitably inert organic solvent with stirring, shaking, or agitation to form a protected tyrosine containing dipeptide. Introducing this dipeptide to appropriate protecting group removal conditions affords a selectively deprotected dipeptide which is well-suited for continued peptide synthesis. Contacting this mono-deprotected tyrosine containing dipeptide with an appropriately protected amino acid having a side chain represented as above, in the presence of a suitable peptide coupling agent in a suitably inert organic solvent with stirring, shaking, or agitation, forms a protected tyrosine containing tripeptide. This method may be repeated as many times as necessary to achieve the desired peptide.

The method of preparation for peptide synthesis requires specific functional groups to react with other substituents to link amino acid residues in a desired manner to form a peptide possessing a known and desired sequence of amino acid residues. Since amino acids possess at least two reactive functional groups, suitable protection, blocking, or masking of these groups is required to ensure that reaction will occur only at specifically desired sites.

These protecting groups should be introduced to the moiety efficaciously while their removal should be performed under conditions which do not affect other portions of the molecule. In this manner, certain reactions and modifications may be performed on the amino acid, peptide, or other compound, with assurance that the protected functionality will not interfere with the desired reaction. Further, by choosing a protecting group that is sensitive and labile to certain reactive conditions, a reaction scheme may be outlined to advantageously utilize these characteristics to effectively remove the protecting group once the synthesis is complete.

Both N-protecting groups and COOH-protecting groups (see definitions) may be used within the scope of this invention. A variety of protecting groups known in the field of peptide synthesis and recognized by conventional abbreviations therein, may be found in T. Greene, *Protective Groups In Organic Synthesis,* Academic Press (1981). Among the preferred protecting groups that may be utilized for suitable protection of reactive nucleophilic substituents include, for example, benzyl (Bz), carbobenzyloxy (Cbz), t-butoxycarbonyl (Boc), or 9-fluorenylmethyloxy-carbonyl (Fmoc).

Coupling of amino acids, which may be the same or different as those described above, to yield small peptides in route to peptides comprised of greater numbers of amino acid residues may be accomplished by employing established techniques in the field of peptide chemistry. A broad range of suitable reactions are described in E. Gross and J. Meinhofer, *The Peptides: Analysis, Synthesis, Biology; Modern Techniques of Peptide and Amino Acid Analysis,* John Wiley & Sons, (1981) and M. Bodanszky, *Principles Of Peptide Synthesis,* Springer-Verlag (1984). The peptide coupling agents which may be used to assist condensation of amino and carboxylic acid moieties include N,N'-dicyclohexylcarbodiimide (DCC), N,N'-carbonyl diimidazole (CDI), 1-hydroxy benzotriazole (HOBt), ethyl chloroformate, benzyl chloroformate, 1-(ethoxycarbonyl)-2-ethoxy-1,2-dihydroquinoline (EEDQ), benzotriazoyl-oxy-tris-(dimethyl)amino-phosphonium hexafluoro phosphate (BOP) and the like. A preferred technique uses DCC as the coupling reagent. The DCC method may be used with or without catalytic additives such as 4-dimethylaminopyridine (DMAP), copper (II) chloride or HOBt to hasten the reaction and suppress the racemization of the desired compound.

The DCC reaction is often performed at room temperature but may be carried out from about −78° C. to gentle reflux in a variety of solvents that are inert with respect to the reactants. The solvents are normally organic solvents which are polar and aprotic. Preferred solvents include, for example, dichloromethane, chloroform, diethyl ether, tetrahydrofuran (THF), N,N'-dimethylformamide (DMF), and the like. Particularly preferred solvents are dichloromethane and DMF. In general, the coupling reaction may be carried out at atmospheric pressure a temperature of −78° C. to reflux for a period of between 1 and 48 hours. Preferably, the reaction is carried out at about −10° C. to 25° C. with stirring, shaking or agitation, over a period of between 4 and 6 hours.

Alternatively, synthesis may be achieved using solid phase synthesis, such as that described by Merrifield, J. Am. Chem. Soc., 85, p 2149 (1964), although other equivalent chemical syntheses known in the art can also be used. Solid-phase synthesis is commenced from the C-terminus of the peptide by coupling a protected alpha-amino acid to a suitable resin as generally set forth in U.S. Pat. No. 4,244,946.

As an example, Ile protected by BOC is coupled to the a BHA resin using methylene chloride and dimethylformamide. Following the coupling of BOC-Ile to the resin support, the alpha-amino protecting group is removed, as by using trifluoroacetic acid (TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, *The Peptides,* pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide (DCC) and N,N'-diisopropyl carbodiimide (DICI), or N-ethyl-N'-(3-dimethylaminopropyl) carbodiimide. Other activating reagents and their use in peptide coupling are described by Schroder & Lubke, supra, in Chapter III and by Kapoor (1970) J. Phar. Sci. 59:127.

Each protected amino acid or amino acid sequence is introduced into the solid phase reactor in about a fourfold excess, and the coupling is carried out in a medium of dimethylformamide: dichloromethane (1:1) or in DMF or dichloromethane alone. In instances where the coupling is carried out manually, the success of the coupling reaction at each stage of the synthesis is monitored by the ninhydrin reaction, as described by E. Kaiser et al. (1970) Anal. Biochem. 34:595. In cases where incomplete coupling occurs, the coupling procedure is repeated before removal of the alpha-amino protecting group prior to the coupling of the next amino acid. The coupling reactions can be performed automatically, as on a Applied Biosystems automatic synthesizer.

After the desired amino acid sequence has been completed, the intermediate peptide is removed from the resin support by treatment with a reagent, such as liquid hydrogen fluoride, which not only cleaves the peptide from the resin but also cleaves all remaining sidechain protecting groups and the alpha-amino protecting group (unless it is an acyl group which is intended to be present in the final peptide) to obtain the peptide. When using hydrogen fluoride for cleaving, anisole or cresol and methylethyl sulfide are included in the reaction vessel as scavengers. When Met is present in the sequence, the BOC protecting group may be cleaved with trifluoroacetic acid (TFA)/ethanedithiol prior to cleaving the peptide from the resin to eliminate potential S-alkylation.

All patents and publications referred to in the examples, and throughout the specification, are incorporated herein by reference, without admission that such is prior art.

The following nonlimiting examples are provided to illustrate the invention. The skilled artisan will recognize that there may be substitutions and variations of the exemplified methods and compositions which are apparent and can be practiced without departing from the essence of the invention.

EXAMPLES

Example 1

Peptide Synthesis

The synthesis of the peptide of SEQ ID NO:1 (Thr-Ile-Glu-Asp-Ser-Tyr-Arg-Lys-Gln-Val-Val-Ile-Asp) is conducted in a stepwise manner on a MBHA hydrochloride resin, such as available from Bachem, Inc. (Torrance, Calif.) having a substitution range of about 0.1 to 0.5 mmoles/gm. resin.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All solvents used in the peptide preparations described herein, e.g. methylene chloride dichloromethane, 2-propanol, dimethylformamide (DMF), and methanol, were Burdick and Jackson "distilled in glass" grade and used without additional distillation. Trifluoroacetic acid (TFA), diisopropylethylamine (DIPEA), piperidine (PIP), dicyclohexylcarbodiimide (DCC), 1-hydroxybenzotriazole (HOBt), and [benzotriazole-1-yl-oxy-tris(dimethyl) phosphonium hexafluorophosphate] (BOP) were purchased from Chemical Dynamics Corp. and were "sequenal" grade purity. 1,2-ethanedithiol (EDT) was purchased from Sigma Chemical Co. and used without further purification. All protected amino acids were of the L-configuration unless otherwise indicated and were obtained from Bachem (Torrance, Calif.).

The synthesis is performed on an Applied Biosystems peptide synthesizer (Foster City, Calif.) using a suitable program, preferably as follows:

| STEP | REAGENTS AND OPERATIONS | MIX TIMES |
|---|---|---|
| 1 | Dichloromethane - 80 ml. | 2 |

-continued

| STEP | REAGENTS AND OPERATIONS | MIX TIMES |
|---|---|---|
| 2 | Methanol (MeOH) wash - 30 ml. | 2 |
| 3 | Dichloromethane - 80 ml. | 3 |
| 4 | 50 percent TFA plus 5 percent 1,2-ethane-dithiol in dichloromethane - 70 ml. | 2 |
| 5 | Isopropanol wash - 80 ml. | 2 |
| 6 | TEA 12.5 percent in dichloromethane - 70 ml. | 2 |
| 7 | MeOH wash - 40 ml. | 2 |
| 8 | Dichloromethane wash - 80 ml. | 3 |
| 9 | Boc-amino acid (10 mmoles) in 30 ml. of either DMF or dichloromethane, depending upon the solubility of the particular protected amino acid, (1 time) plus DCC (10 mmoles) in dichloromethane (reaction time 20–200 min) | |

Note:
All wash and mix times three minutes except where noted.

Coupling of BOC-ASP(OBz) results in the substitution of about 0.35 mmol ASP per gram of resin. All solvents that are used are carefully degassed, preferably by sparging with an inert gas, e.g., helium or nitrogen, to insure the absence of oxygen.

After deprotection and neutralization, the peptide chain is built stepwise on the resin. Generally, one to two mmol. of BOC-protected amino acid in methylene chloride is used per gram of resin, plus one equivalent of 2M DCC in methylene chloride, for two hours. When BOC-Arg(Tos) is being coupled, a mixture of 50% DMF and methylene chloride is used. Bzl is used as the hydroxyl side-chain protecting group for Ser and Thr. p-nitrophenyl ester (ONp) can be used to activate the carboxyl end of Asn or Gln; for example, BOC-Asn(ONp) can be coupled overnight using one equivalent of HOBt in a 50% mixture of DMF and methylene chloride. The amido group of Asn or Gln is protected by Xan when DCC coupling is used instead of the active ester method. 2-Cl-CBZ is used as the protecting group for the Lys side chain. Tos is used to protect the guanidine group of Arg and the imidazole group of His, and the side-chain carboxyl group of Glu or Asp is protected by OBzl.

To cleave and deprotect the resulting protected peptide-resin, it is treated with 1.5 ml anisole, 0.5 ml of methylethylsulfide and 15 ml liquid hydrogen fluoride (HF) per gram of peptide-resin, first at −20° C. for 20 min and then at 0° C. for 30 min. This reaction must be performed with great care owing to the highly toxic and corrosive nature of hydrogen fluoride. This reaction is performed in a commercially available teflon apparatus (Penninsula Research, Inc., Richmond, Calif.). After complete elimination of HF under high vacuum using a KOH trap, the resin-peptide is washed alternately with dry diethyl ether and chloroform, and the peptides are then extracted with degassed 2N aqueous acetic acid and separated from the resin by filtration on a Hirsch funnel.

The peptide is purified by gel permeation followed by preparative HPLC as described in Marki et al. (1981) J. Am. Chem. Soc. 103:3178; Rivier, et al. (1984) J. Chromatography 288:303–328; and Hoeger, et al. (1987) BioChromatography 2:134–142. The chromatographic fractions are carefully monitored by HPLC (see below), and only the fractions showing substantial purity are pooled.

To confirm that the desired sequence is achieved, the peptide is hydrolyzed in sealed evacuated tubes containing constant boiling HCl, 3 μl of thioglycol/ml and 1 nmol of Nle (as an internal standard) for 9 hours at 140° C. Amino acid analysis of the hydrolysates using a Beckman 121 amino acid analyzer to determine amino acid ratios allows confirmation that the desired peptide structure has been obtained.

Example 2

Cyclization of Active Peptides

Cyclization "traps" the bioactive conformation of the peptide by making the active conformation part of a ring system that allows it much less conformational flexibility. In this procedure, aspartate or glutamate residues are introduced into the sequence either in place of non-essential amino acid residues or as added residues in the chain. The new peptide is then subjected to electro-oxidation in which the two residues are decarboxylated, in an intramolecular Kolbe electro-oxidative coupling reaction, resulting in the joining of their respective —$CH_2$ groups, forming a ring as shown in FIG. 1. This method has been used to make a cyclized β-bend of the dipeptide, Pro-Gly, by placing a glutamic acid residue on the amino and carboxyl ends of this dipeptide and then performing the Kolbe electro-oxidation to form the tetra-($CH_2$)-bridge. The Pro-Gly peptide, which has a variety of conformations in solution, when cyclized, was found to adopt the β-bend structure uniquely (Joran, A., "Conformationally restricted biologically active peptides, methods for their production and uses thereof," U.S. Pat. No. 5,364,851.) This method has been used quite recently to synthesize cyclized forms of the peptide vasopressin; these forms have been tested in an in vitro adenylate cyclase system and have been found to have prolonged half-lives and greater activity than the native peptide. Therefore, this cyclization procedure may result in enhanced peptide inhibition and in increased half-life. Introduction of the cyclizing rigidifying agent reduces the flexibility of the peptide and concurrently introduces non-polar aliphatic groups into the peptide (such as the tetra-methylene bridge shown in Scheme I) that help promote transport of the peptide through the cell membrane.

Scheme I illustrates an exemplary result of using electrolytic decarboxylation to cyclize peptides to trap them in their active conformations. Either two glutamate, two aspartate, or one glutamate and one aspartate residues are introduced in the chain represented by the wavy line. Under electro-oxidation shown here for two glutamate residues, a tetramethylene bridge forms cyclizing the region of the peptide that is to be held fixed in its bioactive conformation. The two connected residues shown constitute the diamino suberic acid moiety.

Scheme I

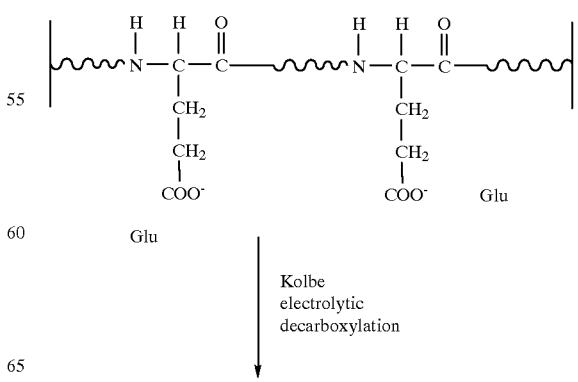

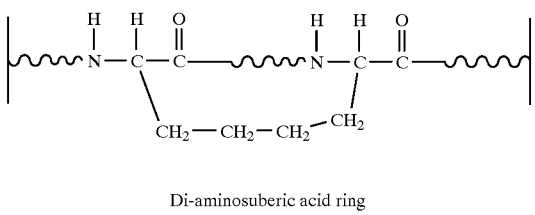

Di-aminosuberic acid ring

It should be noted that, in the synthesis of this new peptide, there are possibly other aspartate and glutamate amino acid residues that can undergo the oxidative decarboxylation. To prevent these reactions from occurring, these Asp and Glu residues are protected as esters during the solid phase synthesis of the peptide. The free Glu residues at positions 44 and 46 are then allowed to undergo the cyclization reaction, after which the protected acid groups are then deprotected.

This cyclization procedure can be performed on other regions of this peptide and on the other two active peptides.

The electrooxidative coupling reaction used to prepare the cyclic peptides of the invention can be performed in a divided or an undivided cell such as a standard glass H-cell, as described in *Organic Electrochemistry* (2nd Ed.), M. Baizer and H. Lund, eds., Marcel Dekker, N.Y., 1983, Chap. 5, p 168. For large scale runs, the reaction can be carried out in a plate and frame flow cell as described in *Technique of Electroorganic Synthesis*, Part III, N. Weinberg and B. Tilak, ed., John Wiley & Sons, New York, 1982, Chap. III, p 179.

Cathode materials useful for the preparation of the compounds of the invention include, but are not limited to, high hydrogen overvoltage materials such as mercury, lead or cadmium. Anode materials include, but are not limited to, materials such as mercury, lead, graphite, or graphite paste, which are stable under electrolysis conditions.

The electrooxidative coupling can occur in aqueous, or aqueous organic electrolytes, comprising solutions of Bronsted acids, such as sulfuric, fluoroboric, and trifluoroacetic acids. Any electrolyte may be selected that has sufficient acid strength to render a basic starting material protonated. A dilute solution of trifluoroacetic acid is most preferred.

Although the preferred method of electrolysis to obtain the compounds of this invention takes place under constant current conditions, the oxidative coupling could also be performed using controlled potential electrolysis, as understood by those skilled in the art. Typical current densities are between 1 and 5000 milliamps (mA)/cm$^2$, preferably between 10 and 100 mA/cm$^2$. The reaction is preferably carried out at a temperature in the range of about 0° C. to 37° C., more preferably about 10° C.

A standard glass H-cell (200 ml volume, glass frit separator) was equipped with a mercury pool cathode 12 cm$^2$ area), a magnetic stirrer, and a platinum foil anode. The cell reservoir was filled with 40 mM trifluoroacetic acid (110 ml) and placed in a water bath maintained at 10° C. The catholyte was purged with nitrogen. The starting peptide (20 mg) was added to the catholyte and constant current electrolysis was initiated at 0.1 A. The reaction progress was followed by HPLC and after passage of 1,060 coulombs, all the substrate had been consumed and the electrolysis was terminated. The catholyte was recovered and adjusted to pH 8 with NaOH. The pH-adjusted catholyte was extracted with chloroform (2 times 70 ml). The extract was freeze dried and the resultant powdery material extracted with acetonitrile (HPLC grade). This was filtered through a sintered-glass filter (fine porosity) and was reduced in volume on a rotary evaporator using a mechanical vacuum pump to a volume of 2 ml. This material was purified by reversed-phase high pressure liquid chromatography using a Waters HPLC system with a 0.46×0.25 cm column packed with 5 μm C$_{18}$ silica, 300 Å pore size. Buffer A is an aqueous 0.1% (vol/vol) trifluoroacetic acid solution (1.0 ml of TFA per 1000 Ml solution); Buffer B is 100% acetonitrile. The determination is run at room temperature with a gradient from 15.5% Buffer B to 75% Buffer B over a 30 min. The flow rate is 2.2 ml per minute, and the retention time is 25.0 min.

The structure was confirmed by 300 MHz $^1$H NMR, $^{13}$C NMR, and electrospray mass spectroscopy.

The amounts of the reactants and the conditions required to facilitate reaction and encourage efficient completion of the aforementioned Examples may vary widely. However, in general, the amounts of material employed to induce reaction in the processes discussed above will be substantially stoichiometric, unless otherwise specified. In the following examples, reaction concentrations are generally held at 0.1M for the reactants, unless a higher concentration or dilution would be particularly useful for influencing the direction of a specific reaction. In practice, the amounts used will depend upon variations in reaction conditions and the nature of the reactants as readily apparent to one of ordinary skill in the art.

In any of the methods described hereinabove, the desired products may be isolated from the reaction mixture by crystallization. Alternatively, chromatographic techniques including, but not limited to, normal phase, reverse phase, ion-exchange, affinity, or gel permeation, may be employed, as well as electrophoresis or extraction or other means.

Example 3

Oocyte Maturation Assay

Using the method described in Chung et al. (1991) Anticancer Res. 11:1373–1378, test peptides, cyclized peptides and/or peptidomimetics are injected into immature oocytes at various doses. The oocytes are co-injected with recombinant transforming ras p21 obtained from the National Cancer Institute of Japan. Alternatively, the oncogenic ras p21 can be prepared by the ordinary skilled artisan without the expense of undue experimentation as described in Chung et al. (1991) supra and in Chung et al. (1992) *Exp. Cell. Res.* 203:329–335 The maturation of the oocytes is evaluated microscopically at low power (20×), using a Nikon Diaphot microscope, for example. Percent inhibition is calculated based on comparisons with oocytes which are injected with 0.05 mg/ml oncogenic ras p21.

The following results were obtained using a dose of each peptide equivalent to an internal oocyte concentration of 50 nM:

| Peptide | OR | Sequence ID Number | Present Inhibition of ras-Induced Maturation |
|---|---|---|---|
|  |  | 6 | 28 |
| Val—Val—Ile |  |  | 34 |
|  |  | 7 | 56 |
| Lys—Arg—Val |  |  | 22 |
|  |  | 1 | 76 |

-continued

| Peptide | OR Sequence ID Number | Present Inhibition of ras-Induced Maturation |
|---|---|---|
| | 8 | 92 |
| | 2 | 38 |
| | 9 | 65 |
| | 4 | 22 |

The peptidomimetics and cyclic peptides of the present invention will be similarly effective in inhibiting oocyte maturation in response to the oncogenic ras p21 protein, and in inhibiting oncogenesis.

Example 4

Synthesis of Peptidomimetic p21 ras Inhibitor

A representative peptidomimetic of the present invention is synthesized according to Scheme II, as further described hereinbelow.

Scheme II

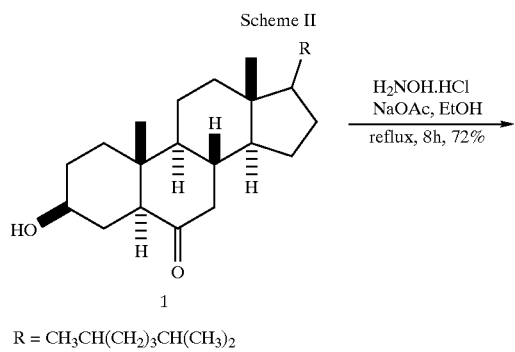

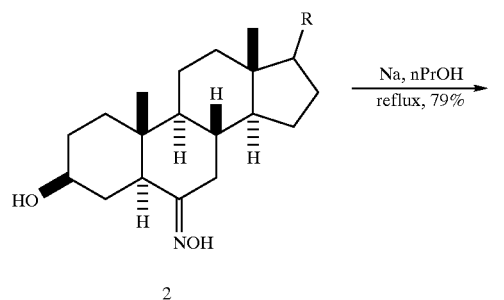

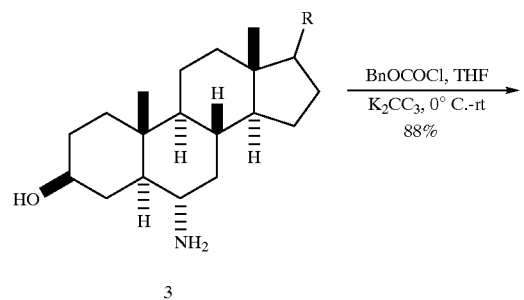

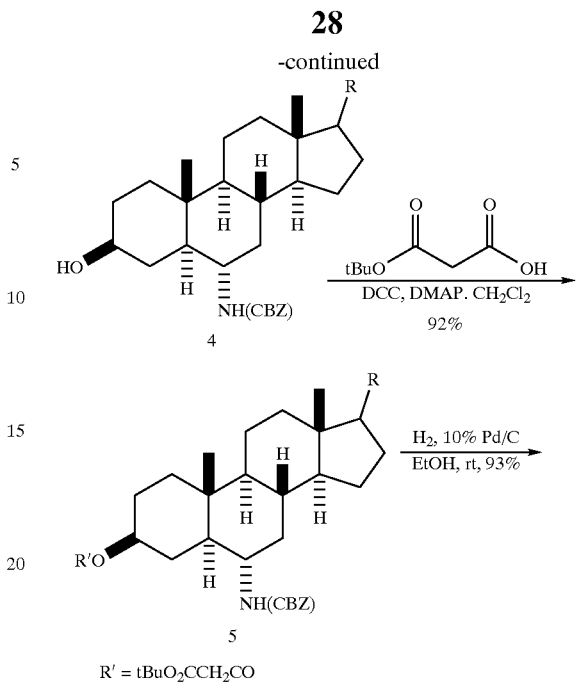

Steroid 1 was commercially available, and used without further purification. Mono-t-butylmalonate was prepared by literature methods [Brunwin, D. M.; et al. (1971) *J. Chem. Soc. C.* 3756]. THF was distilled from sodium/benzophenone under Ar. Methylene chloride and ethanol (absolute) were distilled from CaH2 under Ar. Benzylchloroformate and n-propyl alcohol are commercially available, and used without further purification or drying. All reactions performed under an atmosphere of Ar unless otherwise noted.

5-α-3-β-hydroxy-6-oximinocholestane (2)

Cholestanone 1 (1.00 g. 2.5 mmol), NaOAc (352 mg, 4.3 mmol) and hydroxylamine hydrochloride (197 mg, 2.8 mmol) were heated at reflux in absolute ethanol (15 ml). The reaction was efficiently stirred under Ar for 11 h at reflux. The reaction was cooled, and the solvent removed on the rotary evaporator. The resulting white solid was dissolved in $CHCl_3$, and washed once with brine (80 ml). The organic layer was dried over $Na_2SO_4$, filtered, and concentrated in vacuo. The yield of crude material was 1.068 g of a lightly colored solid. The material was recrystallized from absolute ethanol (15.5 mL) to give 752 mg (72%) of white needles, mp=202–204° C. (dec). $^1H$ NMR($CDCl_3$): δ3.60 (m, 1H), 3.33 (dd, J=4.37, 13.6 Hz, 1H), 2.10–1.75 (broad m, 6H), 1.70–1.45 (broad m, 5H), 1.42–1.28 (broad m, 8H), 1.14 (m, 9H), 0.92 (d, J=6.87 Hz, 3H), 0.88 (d, J=6.54 Hz, 6H), 0.77 (s, 3H), 0.67 (s, 3H). $^{13}C$ NMR ($CDCl_3$): δ159.55, 70.77, 56.39, 55.91, 54.04, 49.26, 42.60, 39.42, 39.20, 38.57, 35.92, 35.84, 35.63, 35.43, 31.24, 30.40, 29.39, 27.87, 27.70, 23.80, 23.53, 22.51, 22.26, 21.17, 18.36, 12.34, 11.79, IR (neat film) : 3354, 2941, 1667, 1467, 1065, 978 cm$^{-1}$.

5-α-6-α-amino-3-β-hydroxycholestane (3)

Oxime 2 (752 mg, 1.8 mmol) was dissolved with good stirring in boiling n-propyl alcohol (32 mL). The flask was removed from the oil bath, and small pieces of freshly prepared sodium wire (2.898 g, 126 mmol) were added at a rate sufficient to maintain the reflux. After the addition of the sodium was complete, the flask was lowered into the bath, and stirred at reflux for 2 h (a thick, white crust forms). The reaction was cooled to room temperature, and carefully quenched by slow, dropwise addition of water under an inert atmosphere. The quenched reaction was extracted twice with CHCl$_3$ (50 mL), and the extracts were washed with brine, dried over Na$_2$SO$_4$, filtered, and concentrated. The yield of a vanilla colored solid was 723 mg. The material was purified by flash chromatography on silica in CHCl$_3$/MeOH (3:2) to give 577 mg (79%) of a vanilla colored solid. Alternatively, the product can be recrystallized from EtOAc. $^1$H NMR (CDCl$_3$): δ3.59 (m, 1H), 2.60 (dd, J=2.87, 10.35, 20.73 Hz, 1H), 2.09 (d, J=11.79 Hz, 1H), 1.99 (d, J=12.94 Hz, 1H), 1.85 (m, 3H), 1.78–1.45 (broad m, 10H), 1.36 (m, 5H), 1.24–0.96 (m, 9H), 0.89 (m, 10H), 0.83 (s, 3H), 0.77 (m, 2H), 0.67 (s, 3H).

N-(benzyloxy carbonyl)-5-α-6-α-amino-3-β-hydroxycholestane (4)

The amine 3 (465 mg. 1.15 mmol) and anhydrous K$_2$CO$_3$ (457 mg, 3.3 mmol) were stirred in dry THF (4 mL), and cooled to 0° C. in an ice-water bath. Benzyl-chloroformate (0.16 mL, 1.15 mmol) was added dropwise, and the reaction was stirred at 0° C. for 15 min, then at room temperature for 6 h. The reaction was diluted with water and poured into saturated NaHCO$_3$ (15 mL). A thick, flocculent white precipitate formed. The aqueous mixture was extracted with CHCl$_3$ (20 mL), and the aqueous layer was saturated with NaCl and extracted with CHCl$_3$ (5×20 mL). The organic extracts were washed with brine (40 mL), dried over Na$_2$SO$_4$, filtered, and concentrated. The yield of crude material was 649 mg of a tan solid. The material was flash chromatographed on silica in Hex/EtOAc (1:1), (using a little CHCl$_3$ to help dissolve material) to give 546 mg (88%) of a white solid. $^1$H NMR (CDCl$_3$): δ7.88 (m, 4H), 7.23 (s, 1H), 5.08 (d, J=3.08 Hz, 2H), 4.86 (d, J=9.46 Hz, 1H), 3.53 (m, 1H), 3.50 (s, 1H; overlaps with the multiplet at 3.53), 2.00 (d, J=12.35 Hz, 2H), 1.85 (m, 3H), 1.53 (m, 4H), 1.49–1.22 (broad m, 9H), 1.20–0.98 (broad m, 10H), 0.90 (m, 9H), 0.87 (s, 3H), 0.77 (m, 2H), 0.66 (s, 3H). IR (neat film): 3346 (broad), 1691, 1544, 1022 cm$^{-1}$.

N-(benzyloxy carbonyl)-5-α6-α-amino-3-β-mono-t-butyl malonyl cholestane (5)

The amine 4 (144.4 mg, 0.27 mmol), mono-t-butyl malonate (107.7 mg, 0.67 mmol), and DMAP were dissolved in dry CH$_2$CL$_2$ (1.2 mL), and stirred efficiently at room temperature. DCC (67.4 dmg, 0.33 mmol) was added in one portion under a stream of Ar. The reaction was stirred at room temperature for 23 h, then diluted with ether, and filtered through a pad of Celite (a white solid remains on the pad). The filtrate was washed with 10% citric acid (20 mL), saturated NaHCO$_3$ (20 mL), and brine (20 mL). The organic layer was dried over Na$_2$SO$_4$, filtered and concentrated. The yield of crude material was 200 mg. The material was flash chromatographed in Hex/EtOAc (6.7:1) to give 168.7 mg (92%) of a yellow-gold residue $^1$H NMR (CDCl$_3$): δ7.36 (s, 4H), 7.29 (s, 1H), 5.08 (q, J=12.25, 27.09 Hz, 2H), 4.70 (m, 1H), 4.38 (d, J=9.56 Hz, 1H), 3.27 (s, 2H), 2.00 (m, 2H), 1.85 (m, 4H), 1.54 (m, 3H), 1.48 (s, 9H), 1.35 (M, 8H), 1.11 (m, 11H), 0.89 9(m, 12H), 0.75 (m, 2H), 0.66 (s, 3H).

The N-CBZ group of 5 was cleanly removed by hydrogenolysis using 10% palladium on carbon under a hydrogen atmosphere to give 6 in 93% yield. Trials employing 1,4-cyclohexadiene as the hydrogen source [Felix et al. (1978) J. Org. Chem. 43:4194] produced 6 in only 23% yield, even when a large excess of the diene was used. Longer reaction time did not improve the yield.

5-α-6-α-amino-3-β-mono-t-butyl malonyl cholestane (6)

5 (200.7 mg, 0.3 mmol) and 10% palladium on carbon (194 mg) were stirred vigorously in abs. EtOH (1.8 mL). The system was flushed with a balloon of hydrogen, and an atmosphere of hydrogen was maintained by 2 balloons of hydrogen. The reaction was stirred for 20 h at room temperature, then vented with Ar, and suction-filtered through a tightly packed pad of Celite. The flask and filter cake were thoroughly washed with 1:1 EtOH/THF. The filtrate was concentrated in vacuo to give 167.8 mg of material. The crude product was flash chromatographed first in Hex/EtOAc (3:2) to elute off minor byproducts, then CHCl$_3$/MeOH (9:1) to give the product in a yield of 153.3 mg (93%) of a golden residue. $^1$H NMR (CDCl$_3$): δ4.76 (m, 1H) 3.27 (s, 2H), 2.60 (m, 1H), 2.22 (m, 1H), 2.05–1.71 (broad m, 6H), 1.51 (s, 3H), 1.49 (s, 9H), 1.34 (broad m, 8H), 1.24–0.97 (broad m, 12H), 0.92 (d, J=6.55 Hz, 3H), 0.88 (d, J=6.64 Hz, 6H), 0.85 (s, 3H), 0.75 (m, 2H), 0.67 (s, 3H), IR (neat film) : 3368, 2946, 2868, 1747, 1729, 1144, 1008 cm$^{-1}$.

Reductive amination of N(BOC) aminoacetaldehyde [Buchardt et al. (1993) Org. Prep. Proc. Int. 25:457] is promoted by the use of NaBH$_3$CN and catalytic acetic acid. t-Butylester and BOC groups are removed. The general plan is given in Scheme III.

Scheme III

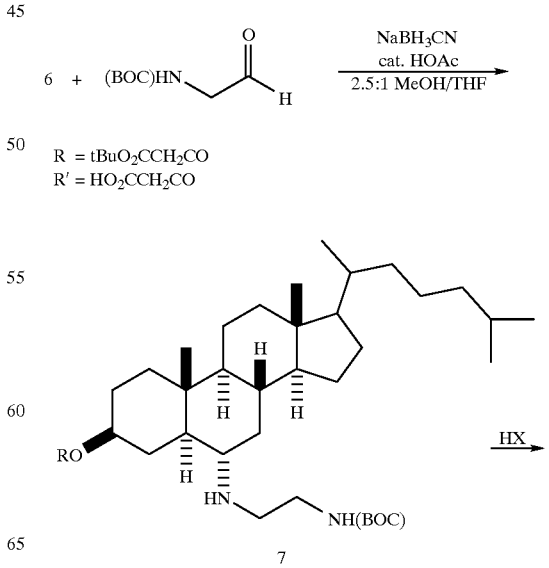

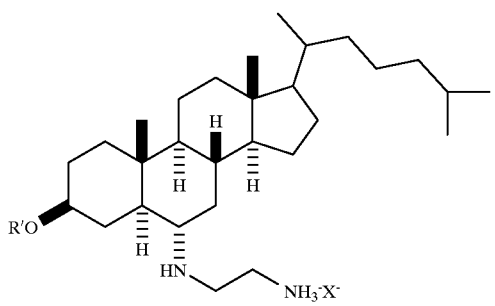

We claim:

1. A peptidomimetic of the structure

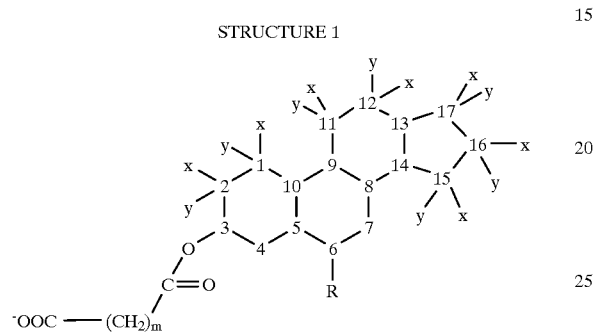

STRUCTURE 1 wherein the sidechain R attached at the carbon atom numbered 6 on the sterol nucleus can be NH—$CH_2$—$CH_2NH_3^+$ alkyl amino, arylamino, or aralkylamino group, and wherein the sidechain attached at the carbon number 3 can be replaced with —O—C(=O)——$(CH_2)_m$—COOH, where m is an integer from 1 to 6, inclusive, and one of x and y at each position independently, can be one H, a small alkyl group of $C_1$ to $C_3$; a halogen, or an amino group where the other of one of x and y is H.

2. The peptidomimetic of claim 1 having a structure

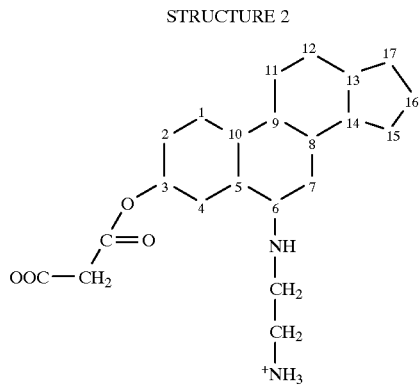

STRUCTURE 2 or a pharmaceutically acceptable salt thereof.

3. A composition comprising at least one peptidomimetic of claim 1 in a pharmaceutically acceptable carrier.

4. The composition of claim 3 wherein said peptidomimetic has a structure

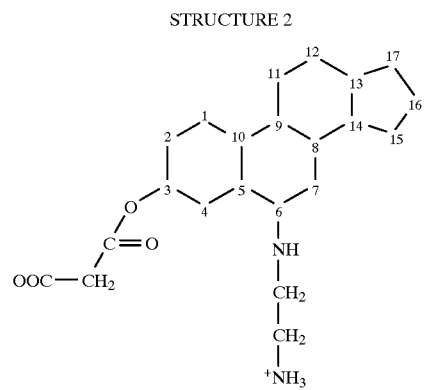

STRUCTURE 2

5. The composition of claim 3 further comprising at least one peptide selected from the group consisting of Val-Val-Ile, Ile-Lys-Arg-Val-Lys-Asp (SEQ ID NO:1), Lys-Cys-Asp-Leu-Ala (SEQ ID NO:2), Cys-Asp-Leu-Ala-Ala-Arg-Thr (SEQ ID NO:3) and Asp-Leu-Ala-Ala (SEQ ID NO:4) or a physiologically acceptable salt of said peptide.

6. The composition of claim 5 wherein said peptidomimetic is 3-malonoxy-6-(2-aminoethyl) aminocyclopentan-operhydrophenanthrene.

7. The composition of claim 3 further comprising at least one cyclized peptide selected from the group consisting of cyclo {-R(1) R(2) Thr-Ile-Glu-Asp-Ser-Tyr-Arg-Lys-Gln-Val-Val-Ile-Asp R(3) R(4)-}, cyclo {-R(1) R(2) Val-Val-Ile R(3) R(4)-}, cyclo {-R(1) R(2) Tyr-Arg-Glu-Gln-Ile-Lys-Arg-Val-Lys-Asp-Ser-Asp-Asp-Val-Pro R(3) R(4)-}, cyclo {-R(1) R(2) Lys-Arg-Val R(3) R(4)-}, cyclo {-R(1) R(2) Ile-Lys-Arg-Val-Lys-Asp R(3) R(4)-}, cyclo {-R(1) R(2) Gly-Asn-Lys-Cys-Asp-Leu-Ala-Ala-Arg-Thr-Val-Glu R(3) R(4)-}, cycle {-R(1) R(2) Lys-Cys-Asp-Leu-Ala R(3) R(4)-}, cyclo {-R(1) R(2) Cys-Asp-Leu-Ala-Ala-Arg-Thr R(3) R(4)-}, cyclo {-R(1) R(2) Asp-Leu-Ala-Ala R(3) R(4)-}, cyclo {, cyclo {-R(1) R(2) D-Thr-Ile-Glu-Asp-Ser-Tyr-Arg-Lys-Gln-Val-D-Val-Ile-Asp R(3) R(4)-}, cyclo {-R(1) R(2) D-Val-D-Val-D-Ile R(3) R(4)-}, cyclo {-R(1) R(2) D-Tyr-Arg-Glu-Gln-Ile-Lys-Arg-Val-Lys-Asp-D-Ser-Asp-D-Asp-Val Pro R(3) R(4)-}, cyclo {-R(1) R(2) D-Lys-D-Arg-)D-Val-R(3) R(4)-}, cyclo {-R(1) R(2) D-Ile-Lys-Arg-Val-Lys-D-Asp-R(3) R(4)-}, cyclo {-R(1) R(2) Gly-D-Asn-Lys-Cys-Asp-Leu-D-Ala-Ala-Arg-Thr-D-Val-Glu R(3) R(4)-}, cyclo {-R(1) R(2) D-Lys-Cys-Asp-Leu-D-Ala R(3) R(4)-}, cyclo -R(1) R(2) Cys-Asp-Leu-Ala-Ala-Arg-D-Thr R(3) R(4)-}, cyclo {-R(1) R(2) Asp-D-Leu-D-Ala-D-Ala R(3) R(4)-}, and

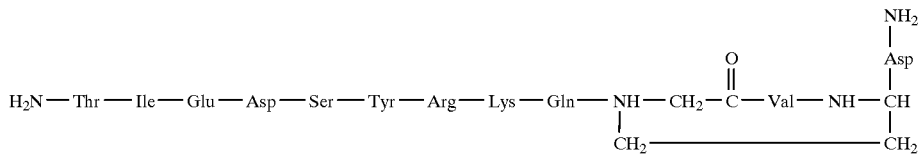

wherein R(1) R(2), R(3) and R(4) represent independently alanine, ornithine, cysteine, lysine, glutamic and aspartic acid, and wherein there is a covalent bond between the carboxyl and amino termini by which R(1) and R(4) are interconnected to each other via a methylene bridge of type —$(CH_2)_m$— or —$(CH_2)_m$—M—$(CH_2)_{m'}$—, wherein m and m' are integers 1, 2, 3, or 4, and M is NH, N{R(5)}, O, or S, and wherein R(5) is methyl, ethyl, n-propyl, isopropyl, cyclopropyl, cyclobutyl, or the sidechain of any naturally occurring amino acid, or a physiologically acceptable salt thereof.

8. The composition of claim 7 wherein said peptidomimetic is 3-malonoxy-6-(2-aminoethyl) aminocyclopentanoperhydrophenanthrene.

* * * * *

UNITED STATES PATENT AND TRADEMARK OFFICE
CERTIFICATE OF CORRECTION

PATENT NO. : 5,910,478

DATED : June 8, 1999

INVENTOR(S) : Hlavka et al.

It is certified that error appears in the above-identified patent and that said Letters Patent is hereby corrected as shown below:

In Column 4, line 44, please insert --H.-- after "is".
In Column 4, line 56, please delete "OOC" and replace with --⁻OOC--.
In Column 7, line 15, please delete "$\sigma_{ij}$" and replace with --$\rho_{ij}$--.
In Column 10, line 46, please delete "R-IX," and replace with --I-IX,--.
In Column 10, line 61, please delete "$(CH_2)_{m'}$." and replace with --$(CH_2)_{m'}$--.--
In Column 12, line 27, please insert --(-- before "$CH_2)_m$"
In Column 12, line 48, please delete "OOC" and replace with --⁻OOC--.
In Column 29, line 54, please insert a dash between "α" and "6".
In Column 97, line 54, please delete "OOC" and replace with --⁻OOC--.
In Column 98, line 24, please delete "OOC" and replace with --⁻OOC--.
In Column 98, line 52, please delete "cycle" and replace with --cyclo--.
In Column 98, line 55, please delete "cyclo {,".
In Column 98, line 59, please delete ")" directly before the "D" at the end of the line.

Signed and Sealed this

Ninth Day of November, 1999

Q. TODD DICKINSON

Attest:

Attesting Officer

Acting Commissioner of Patents and Trademarks